US008993835B2

(12) United States Patent
Langham

(10) Patent No.: US 8,993,835 B2
(45) Date of Patent: *Mar. 31, 2015

(54) PYGMY SESAME PLANTS FOR MECHANICAL HARVESTING

(71) Applicant: Sesaco Corporation, Austin, TX (US)

(72) Inventor: Derald Ray Langham, San Antonio, TX (US)

(73) Assignee: Sesaco Corporation, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/191,732

(22) Filed: Feb. 27, 2014

(65) Prior Publication Data

US 2014/0182008 A1  Jun. 26, 2014

Related U.S. Application Data

(63) Continuation of application No. 12/769,475, filed on Apr. 28, 2010, now Pat. No. 8,664,472.

(51) Int. Cl.
| *A01H 1/00* | (2006.01) |
| *A01H 1/02* | (2006.01) |
| *A01D 45/30* | (2006.01) |
| *A01H 5/10* | (2006.01) |

(52) U.S. Cl.
CPC ........ *A01H 1/02* (2013.01); *A01D 45/30* (2013.01); *A01H 5/10* (2013.01)
USPC ........................................................ 800/260

(58) Field of Classification Search
None
See application file for complete search history.

(56) References Cited

U.S. PATENT DOCUMENTS

| 6,100,452 | A | 8/2000 | Langham | |
| 6,781,031 | B2 * | 8/2004 | Langham | 800/260 |
| 6,815,576 | B2 | 11/2004 | Langham | |
| 7,148,403 | B2 | 12/2006 | Langham | |
| 7,332,652 | B2 | 2/2008 | Langham | |
| 7,847,149 | B2 | 12/2010 | Langham | |
| 7,855,317 | B2 | 12/2010 | Langham | |
| 7,964,768 | B2 | 6/2011 | Langham | |
| 8,003,848 | B2 | 8/2011 | Langham | |
| 8,058,503 | B1 | 11/2011 | Langham | |
| 8,080,707 | B2 | 12/2011 | Langham | |
| 8,207,397 | B1 | 6/2012 | Langham | |
| 8,507,750 | B1 | 8/2013 | Langham | |
| 8,581,026 | B1 | 11/2013 | Langham | |
| 8,581,028 | B2 | 11/2013 | Langham | |
| 8,586,823 | B1 | 11/2013 | Langham | |
| 8,656,692 | B2 | 2/2014 | Langham | |
| 8,664,472 | B2 | 3/2014 | Langham | |

FOREIGN PATENT DOCUMENTS

| WO | WO9915681 | 4/1999 |
| WO | WO0013488 | 3/2000 |

OTHER PUBLICATIONS

Ashri, A.1998."Sesame Breeding," Plant Breeding Rev. 16:179-228.
Ashri, A. 1980. "Sesame," Oil Crops of the World, Chap. 18, pp. 375-387; McGraw-Hill Publishing, Co., New York.
Bakheit, et al. 1996. "Inheritance of Some Qualitative and Quantitative Characters in Sesamum idicum L," Assuit Journal of the Agricultural Sciences 27:27-41.
Day, Jamie. 1998 "The mechanism of indehiscence in Sesame. Features that might be useful in a breeding programme," Third FAO/IAEA Research Coordination meeting on Induced Mutations for Sesame Improvements, Bangkok, Thailand; Apr. 6-19, 1998; 11pp.
Delgado, et al. 1992. "Analisis Del Cruzamiento Dialelico De Seis Variedades Indehiscentes Y Dos Dehiscentes de Ajonjoli Sesamum indicum L." Agronomia Tropical 42:191-210.
Hutson, B.D. 1983. "Standards for the inspection and grading of sesame seed," Hutson Laboratories, Yuma, Arizona, pp. 1-5.
IBPGR Secretariat. 1981. "Descriptor for Sesame," International Board for Plant Genetic Resources, Rome, pp. 1-19.
Kalton, R.R. 1949. "A promising new oilseed crop for Texas," Proc First International Sesame Conference, Clemson Agricultural College, Clemson, South Carolina, pp. 62-66.
Langham, D.R. 2007. "Phenology of Sesame," Issues in New Crops and New Uses, Janick & Whipkey, eds., ASHS Press, Alexandria, VA, pp. 144-182.
Langham, D.G. 1944. "Natural and controlled pollination in sesame," Journal of Heredity 8:254-256.
Langham, D.G. And Rodriguez, J. 1949. "Improvements in Sesame in Venezuela," Proc. First Intern'l Sesame Conf., Clemson Agri. College, Clemson, South Carolina, pp. 74-79.
Langham, et al. 1956. "Dehiscencia Y otras caracteristicas del ajonjoli, Sesamum indicum L., en relacion con el problema de la cosecha," Gensa, Maracay, Venezuela; pp. 3-16.
Langham, D.R. 1998. "Shatter resistance in Sesame," Third FAO/IAEA Res. Co-ord. Mtng on Induced Mutations for Sesame Improvements, Bangkok, Thailand, Apr. 6-10, 1998; 14 pages.
Langham, D.R. 2001. "Shatter resistance in sesame," In: L. Van Zanten (ed.), Sesame improvements by induced mutations, Proc. Final FAO/IAEA Coordination Research Meeting, IAEA, Vienna TECDOC 1195, pp. 51-61.
Langham, D.R. & Wimers, T. 2002. "Progress in mechanizing sesame in the U.S. through breeding," Trends in Crops and New Uses, J. Janick & A. Whipkey (eds.), ASHA Press Alexandria, VA; pp. 157-173.
Namiki, Mitsuo. 1995. "The Chemistry and Physiological Functions of Sesame," Food Reviews International, 11:281-329.

(Continued)

*Primary Examiner* — Vinod Kumar
(74) *Attorney, Agent, or Firm* — Hemingway & Hansen LLP; D. Scott Hemingway

(57) ABSTRACT

Methods for improved sesame agriculture comprising growing a pygmy sesame line homozygous for the py/py recessive pygmy allele and a character selected from non-dehiscence or improved non-dehiscence are disclosed.

Pygmy sesame plants homozygous for the py/py recessive pygmy allele and a character selected from non-dehiscence or improved non-dehiscence, and a method for breeding the same, are disclosed.

29 Claims, 13 Drawing Sheets

(56) References Cited

OTHER PUBLICATIONS

Osman, H.E. 1985. "Studies in sesame: hybridization and related techiniques," FAO Plant Production and Protection Paper No. 66, pp. 145-156.

"Recommendations for the Discussion Groups," 1995. Proceedings of Sesame Workshop, Darwin and Katherine, Northern Territory, Australia, Mar. 12-23, 1995, pp. 252-257.

Shigeo, et al. 1994. "Breeding of good quality sesame with dehiscence resistance and strong antioxidative property," Baiorunessansu Keikaku (abstract only).

Wongyai, W. & Juttpornpong, S. 1992 Indirect selection for seed weight in sesame using capsule size as a criteria, Sesame and Safflower Newsletter, No. 7, pp. 4-7.

Weiss, E.A. 1971. "History," Castor, Sesame and Safflower, Leonard-Hill Books, London; pp. 311-525.

Weiss, E.A. 1983. "Sesame," Oilseed Crops, Longman Inc., New York, pp. 282-340.

Weiss. 2000. "Sesame," Oilseed Crops, Longman Inc., New York, pp. 131-164.

Yermanos, D.M. 1980. "Sesame," Hybridization of Crop Plants, American Society of Agronomy—Crop Science of America, Madison, Wisconsin, pp. 549-563.

Yermanos, D.M. 1984. "Sesame growing: an idealized overview," Text of speech given in Cairo, Egypt, 4 pages.

Zanten, L.Van (ed.) 1996. "Conclusions and Recommendations," 2nd FAO/IAEA Research Coordination Meeting, Antalya, Turkey, pp. 107-113.

* cited by examiner

```
          /K28p
    D51p              /192
     |          /888
     |          |   \V52
     |        /K0367    /G8
     |        |     \804
     |        |        |    /111
     |        |        \111X
     |    /88B               \BEE
     |    |   |  /G8
     |    |   \S11    /111
     |    |          \111X
     |    |           \BEE
     \ S25
          |       /G8
          |     /804
          |  |   |    /111
          \56B   \111X
                  \BEE
                  /111
                /F822
             \562    \192
                  \700
```

FIG. 6

```
       /K28p
D50p                            /111
 |                           /111X
 |                    /F820        \BEE
 |              /578       \104
 |              |              /104
 |              |          \F853        \192
 |          /031        \118
 |          |        \118
 |      /BI954        /72C
 |       |    |    /L6651        /G8
 |       |    |    |            \804
 |       |    |    |                    /111
 |       |    |    |                \111X
 |       |    |    |                    \BEE
 |       |    |    \2CA    /G8
 |       |    |        \S11    /111
 |       |    |            \111X
 |       |    |                \BEE
 \ S26                        /SOMALIA
   |                     /H6778
   |           /J3208        \118
   |           |    |             /193
   |           |    \H6432    /MAX
   |           |            \076            /R234
   |           |                    \R234 TALL
   |       /K3255                        \BEE
   |        |    |            /G8
   |        |    |        /045
   |        |    |    /H6785    \958
   |        |    |    |        |    /982
   |        |    |    |        \036
   |        |    \J3222        \G53.80-1
   |        |            |            /192
   |        |            |        /195
   |        |            \H6562    \BEE
   \S16                    \701
      |     /G8
      \S11    /111
          \111X
              \BEE
```

FIG. 7

```
        /K28p
  D54p            /G8
   |       /S11   /111
   |        |     \111X
   |        |       \BEE
   |       /88F   /192
   |        |     \888
   |        |     \V52
   |                           /SOMALIA
   |     /BI791         /H6778
   |      |  |     /J3208      \118
   |      |  |      |           /193
   |      |  |      |          \H6432    /MAXIMO
   |      |  |      |                \076          /R234
   |      |  |      |                    \R234 TALL
   |      |  |     /K3255                        \BEE
   |      |  |      |                /G8
   |      |  |      |               /045
   |      |  |      |        /H6785   \958
   |      |  |      |         |        /982
   |      |  |      |         |       \036
   |      |  |     \J3222             \G53.80-1
   |      |  |      |                   /192
   |      |  |      |                  /195
   |      |  |      |           \H6562  \BEE
   |      |  \S16              \701
   |      |  |   /G8
   |      |  |  \S11   /111
   |      |  |         \111X
   |      |  |           \BEE
   \S27   |  |
          /S11   /G8
           |   /S11   /111
           |    |     \111X
           |    |       \BEE
          \S17  /702
              \72A
                \BEE
```

PYGMY SESAME PLANTS FOR MECHANICAL HARVESTING

CROSS REFERENCE TO RELATED APPLICATIONS

This application is a continuation of pending U.S. application Ser. No. 12/769,475 filed Apr. 28, 2010.

STATEMENT REGARDING FEDERALLY SPONSORED RESEARCH OR DEVELOPMENT

Not applicable.

TECHNICAL FIELD

This invention concerns sesame plant breeding and providing sesame plant varieties appropriate for mechanized harvesting.

BACKGROUND OF THE INVENTION

Sesame, or *Sesamum indicum*, is a tropical annual cultivated worldwide for its oil and its nut flavored seeds. The sesame plant has capsules found at its leaf axils, and these capsules which contain the sesame seed. Upon maturity in nature, the capsules holding the sesame seeds begin to dry down, the capsules normally split open, and the seeds fall out. Commercially, the harvester tries to recover as much seed as possible from mature capsules. From ancient times through the present, the opening of the capsule has been the major factor in attempting to successfully collect the seed. Harvesting methods, weather, and plant characteristics all contribute to the amount of seed recovered.

The majority of the world's sesame is harvested manually. With manual non-mechanized methods, it is desirable for the sesame seed to fall readily from the plant. Manual harvesting is labor intensive. Efforts to mechanize or partially mechanize harvesting met with limited success.

A breakthrough was accomplished when non-dehiscent (ND) sesame was developed and patented by Derald Ray Langham. ND sesame was found to possess the proper characteristics which would enable mechanical harvesting without the seed loss disadvantages reported with prior varieties.

U.S. Pat. Nos. 6,100,452; 6,815,576; 6,781,031; 7,148,403; and 7,332,652 each disclose and claim non-dehiscent sesame cultivars having various characteristics.

An improved non-dehiscent sesame (IND) class of sesame was later developed by Derald Ray Langham. IND sesame, through increased constriction, better adhesion between the false membranes, and improved placenta attachment, holds more seed than prior sesame types, as measured four weeks after a crop is ready for harvest (could have been combined). The IND characteristics offer advantages for certain growing applications.

The sesame plant generally grows to a height of about 52-249 cm. Most commercially grown sesame is approximately 120-160 cm in height. Shorter lines of sesame have been reported, but heretofore none have been suitable for total mechanical harvesting.

BRIEF DESCRIPTION OF THE DRAWINGS

FIG. 6 depicts the lineage of D51p.
FIG. 7 depicts the lineage of D50p.
FIG. 8 depicts the lineage of D54p.

DETAILED DESCRIPTION OF THE INVENTION

Pygmy sesame plants suitable for mechanical harvesting, having non-dehiscence (ND) or improved non-dehiscence (IND) are disclosed. Further, methods for breeding the same and methods of use for pygmy sesame having ND or IND characteristics are herein disclosed.

The pygmy lines of sesame disclosed herein define a new category of plant architecture and are suitable for mechanized harvest. Further, the pygmy sesame of the invention is advantageous in methods of sesame crop growing on a large scale. The pygmy sesame lines can be grown in higher populations than taller sesame varieties, are advantageous in mechanized combining processes, are resistant to lodging as compared with taller varieties, reduce the need for weed management, and exhibit a higher harvest index.

The genetic characteristics of the pygmy plant have now been studied through crosses, and it has now been determined that the pygmy allele is PY/py. A sesame plant which phenotypically is pygmy is homozygous for pygmy (py/py). A sesame plant phenotypically normal may be either PY/PY or PY/py. The genetics are further discussed in Table II.

Figure 1:
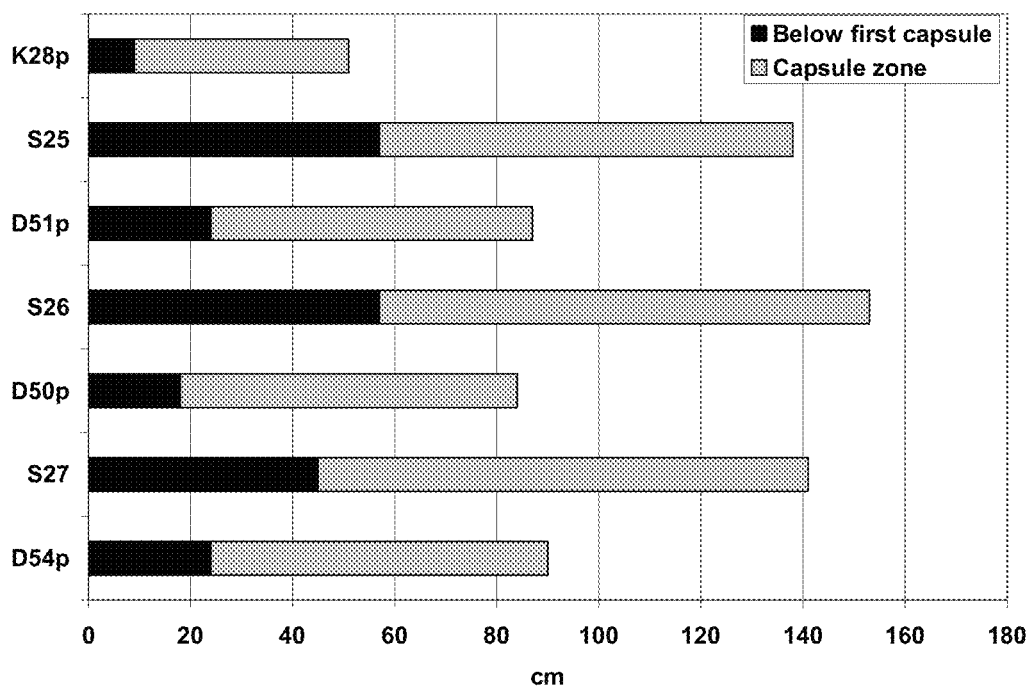
FIG. 1 depicts the plant architecture of seven lines of sesame including a line which contributed pygmy genes (K28p) in a method of breeding pygmy sesame, three Sesaco varieties used as parents (Sesaco 25 "S25", Sesaco 26 "S26", and Sesaco 27 "S27"), and the three pygmy progeny (D50p, D51p, and D54p).

The height of the py/py sesame line of the invention will vary with growing conditions, but generally will be between about 52 and 110 cm. The height of the plant is measured from the ground to the top of the highest capsule with viable seed. (For more details on the character see Table V, Character No. 5. The plant architecture includes the plant height and two other characters discussed below: height of first capsule (Character No. 6) and capsule zone length (Character No. 7). The sum of the two latter characters is the plant height. The plant architecture of seven compared sesame lines is shown in FIG. 1.

The pygmy sesame line described herein has the characteristic of ND or IND. The ND or IND characteristic allows for mechanized harvesting of the crop. In order to impart the ND or IND character to the pygmy line, a sesame line having this character is used in the breeding method. Such sesame lines were disclosed in U.S. Pat. Nos. 6,100,452; 6,815,576; 6,781,031; 7,148,403; and 7,332,652 (non-dehiscent sesame cultivars) which are herein incorporated by reference and U.S. patent application Ser. No. 12/041,257, filed Mar. 3, 2008 (method for breeding improved non-dehiscent sesame (IND)); U.S. patent application Ser. No. 12/041,205, filed Mar. 3, 2008 (improved non-dehiscent sesame cultivar S32, representative seed having been deposited under ATCC accession number PTA-8888); U.S. patent application Ser. No. 12/049,705, filed Mar. 17, 2008 (improved non-dehiscent sesame cultivar S30, representative seed having been deposited under ATCC accession number PTA-8887); U.S. patent application Ser. No. 12/533,972 filed Jul. 31, 2009 (improved non-dehiscent sesame cultivar S27, representative seed having deposited under ATCC accession number PTA-10184), and U.S. patent application Ser. No. 12/565,095, filed Sep. 23, 2009 (non-dehiscent black sesame cultivar S55, representative seed having been deposited under ATCC accession number PTA-10185, which is a stable, commercially suitable sesame line providing the only black sesame that can be mechanically harvested); which applications are herein incorporated by reference as if set forth in their entirety. This application is a continuation of U.S. patent application Ser. No. 12/769,475 filed Apr. 28, 2010, which was filed concurrently with U.S. patent application Ser. No. 12/769,495. U.S. application Ser. No. 12/769,495 issued as U.S. Pat. No. 8,058,503 on Nov. 15, 2011, disclosing a pygmy variety Sesaco 70 (S70) made in accordance with the teachings of the present application, and which is herein incorporated by reference as if set forth in its entirety herein.

The ND and IND lines identified, or other ND or IND lines can be used in breeding a pygmy sesame line to impart such characteristics to the line. The genetics are further explained in Table III.

The ND or IND character is important to the pygmy line. Without ND or IND characteristics, a sesame line is considered "shattering." In order to get an economic yield using shattering lines, a sesame crop has to be manually harvested, which entails cutting it manually at physiological maturity. After manual cutting, the sesame plants are shocked, dried, and then threshed. Threshing involved manually beating the dried cut stalks to separate the sesame seed from the inedible chaff or plant material. Finally, the seed needed to be cleaned away from undesired material.

ND or IND allows for use of machines for all of the harvest process with no manual labor. When manual harvesting is necessary, shorter sesame lines are disadvantageous because harvesting such lines requires an increased level of manual labor and stooping for the workers. Thus, the ND or IND character of the pygmy sesame lines disclosed herein avoid the disadvantage inherent in shorter sesame lines that must be harvested manually.

Because the ND or IND pygmy lines have less shatter, they present an advantage to mechanical harvesting employing a combine. A combine is a farm machine that cuts and threshes grain or other crops in one operation. ("combine" stands for "combined" harvester-thresher). With modern combines the maximum plant height should be under 180 cm, but it is preferred that the varieties be below 150 cm (Langham, D. R. and T. Wiemers, 2002. "Progress in mechanizing sesame in the US through breeding," In: J. Janick and A. Whipkey (ed.), Trends in new crops and new uses, ASHS Press, Alexandria, Va.). With taller plants, the combine reels push the plants forward before pulling them into the combines. Even with shatter resistance, this pushing forward and pulling back shatters seed to the ground. Even when plants are below 150 cm, there is still some shattering caused by the reel.

Pygmy lines produced according to the method disclosed herein are less than about 110 cm in height, have non-dehiscence or improved non-dehiscence, and are more efficiently mechanically harvested than some taller varieties with a farm combine. Preferably, the pygmy lines produced according to the method of the invention are between about 52 cm and 110 cm, most preferably as short as possible while still providing sufficient yield for an economical return.

When the pygmy lines made according to the method of the invention are mechanically harvested with a combine, the reel of the combine brings in the sesame into the cutter bar without first pushing the plants forward. The pygmy lines made according to the invention fall into the header of the combine and are easily fed by the auger into the feeder housing of the combine as illustrated in FIGS. 2-5.

Figure 2:
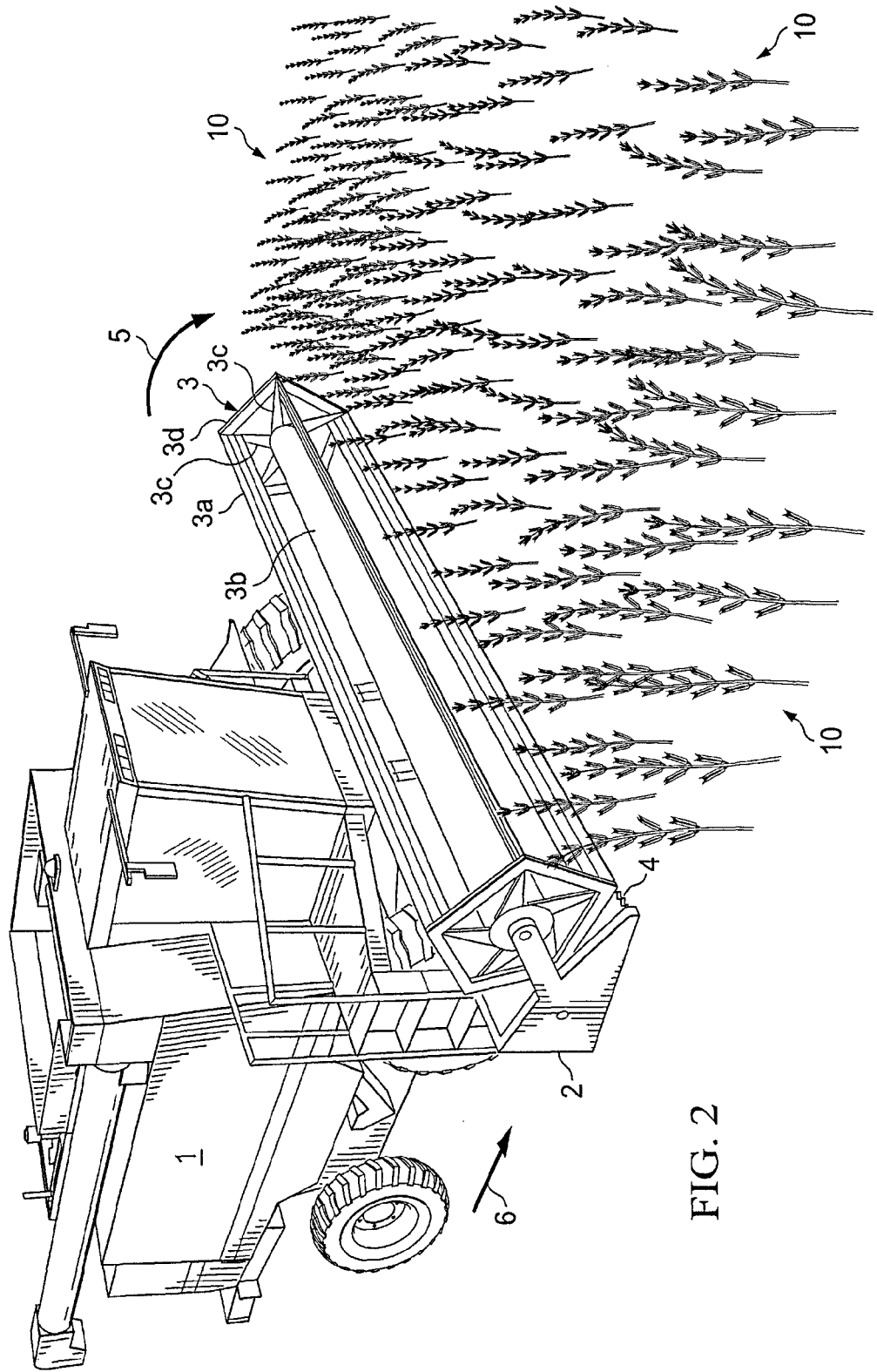
FIG. 2 is a perspective environmental view of a typical farm combine poised to begin mechanical harvesting of sesame plants in the field.

FIG. 2 is a perspective environmental view of sesame plants (10) as grown in a field wherein a combine (1) is ready to begin mechanical harvesting. Standard combine (1) has a platform header (2). The header has a reel (3) that rotates in direction (5) toward the sesame plants (10) growing in a field. The combine platform has a cutter bar (4) which cuts the stems of the plants (10). FIG. 2 is provided for illustrative purposes only, and there has been no attempt to accurately portray the number of sesame plants per square meter. In practice, there can be from 10 to 100 plants per square meter.

Reel (3) illustrated in FIG. 2 has five transverse bars or "bats" (3a). Reel (3) also has center axle (3b) and end frame (3d) which as illustrated is a pentagon shape. End frame (3d) has five spoke-like structures (3c) attached thereto extending essentially radially to center axle (3b). Reels such as Reel (3) as illustrated in FIG. 2 are known as "bat reels" and are the most common type of reel used to mechanically harvest sesame crops.

In practice, combine (1) will be driven by an operator in direction (6) shown in FIG. 2. Reel (3) rotates in direction (5) concurrently. As reel (3) rotates, bats (3a) contact plants (10) and pull them toward header (2) and cutter bar (4) which cuts the plants. Continued rotation of reel (3) pulls the cut plants further into the header (2), and the internal operations of combine (1) (not shown) which separate seed from plant material ("threshing").

Figure 3:
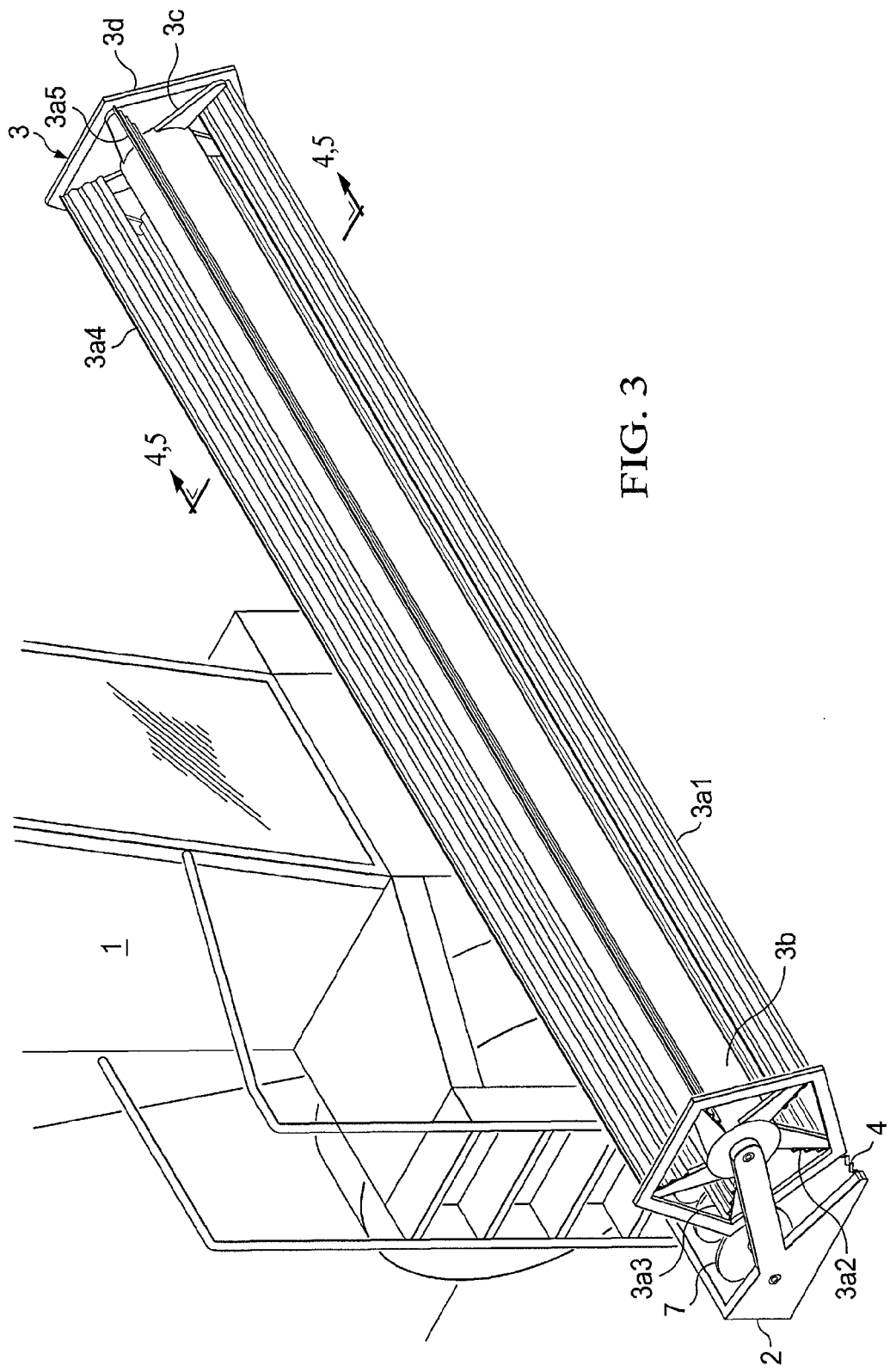
FIG. 3 is a more detailed perspective view of the reel (2) of combine (1) shown in FIG. 2
Figure 4:
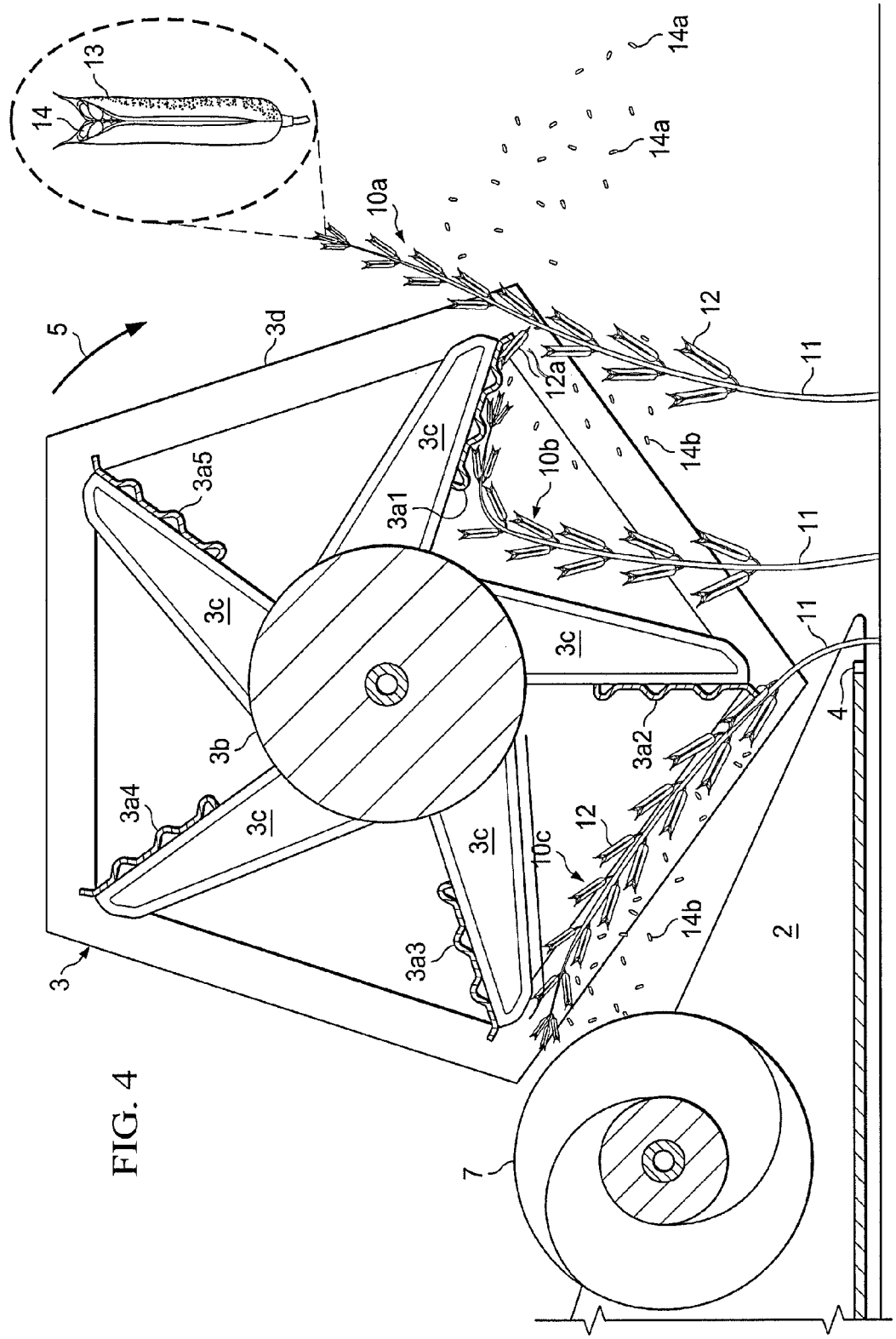
FIG. 4 is a cross section along line 4,5 in FIG. 3 depicting the operation of combine (1) harvesting standard (tall) height non-dehiscent sesame plants (10).
Figure 5:
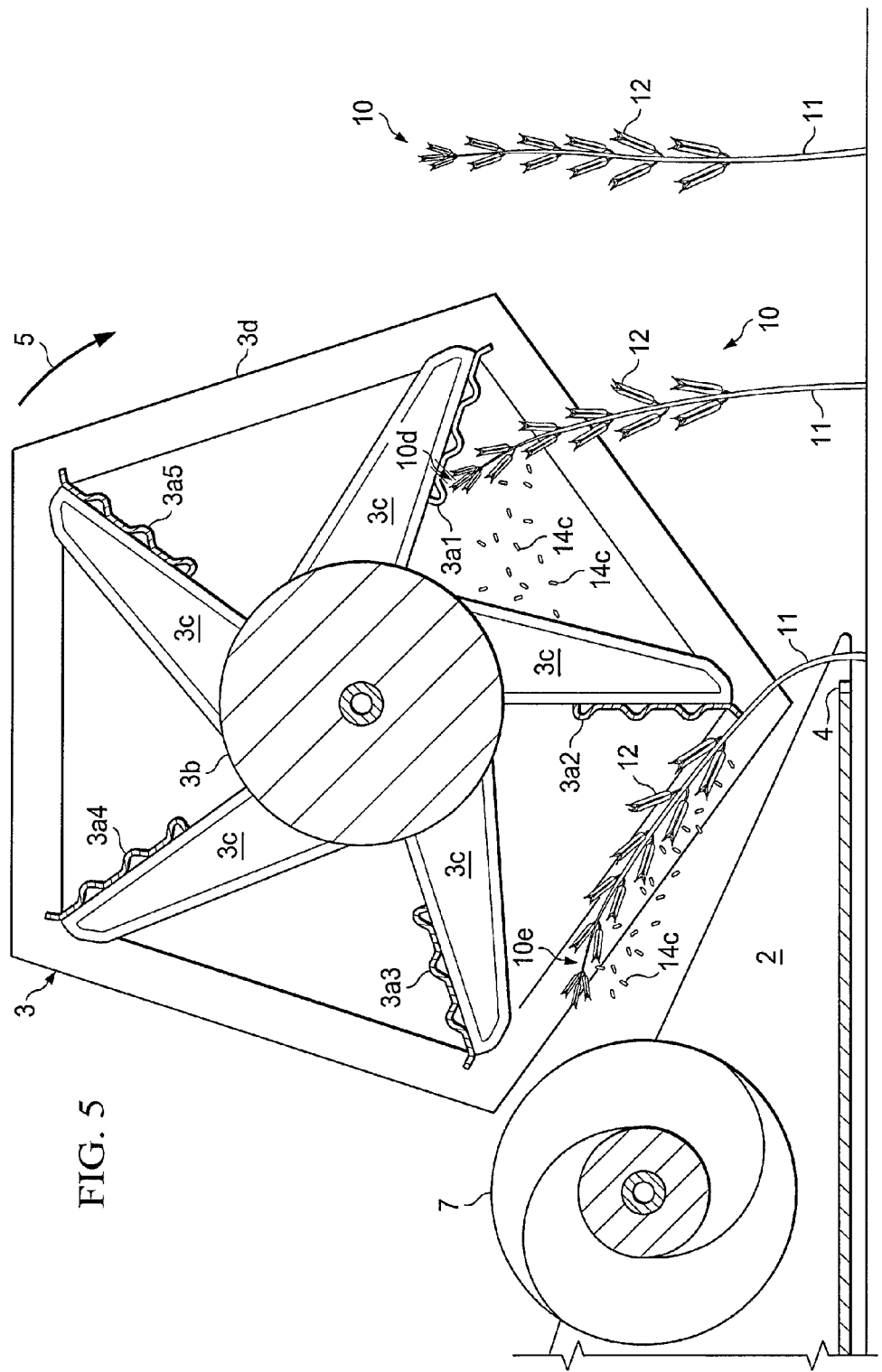
FIG. 5 is a cross section along line 4,5 in FIG. 3 depicting the operation of combine (1) with pygmy non-dehiscent sesame plants (10) of the invention.

FIG. 3 provides a more detailed perspective view of reel (3) of combine (1) to put FIGS. 4 and 5 in context. Here each of the five bats (3a) is individually labeled. Also represented is auger (7) of the header which functions to move the plant material from header (2) into the threshing apparatus (not shown) internal to combine (1). The view for FIG. 4 and FIG. 5 is shown by the 4,5 in FIG. 3.

Now referring to FIG. 4 which illustrates mechanical harvesting of standard (tall) non-dehiscent sesame plants and FIG. 5 which illustrates mechanical harvesting of pygmy non-dehiscent sesame plants in accordance with the present invention. Note that non-dehiscent sesame is required for effective mechanical harvesting, and was developed and patented by the inventor as previously discussed. FIG. 4 and FIG. 5 are cross sectional views of Reel (3) of FIG. 3 along the line indicated in FIG. 3 with representative plants illustrated as they are harvested.

FIG. 4 shows operation of combine (1) with standard (tall) height non-dehiscent sesame plants (10). As previously stated in the context of FIG. 2, reel (3) rotates in direction (5) clockwise towards the plants. The sesame plants (10) have stems (11) and capsules (12). The plants have shed their leaves prior to harvest. Capsules (12) are shown with open tips (13) and exposed seed (14) as best seen in the enlargement of a capsule (12) from plant (10a) provided in FIG. 4. Each capsule (12) contains an average of 70 seeds.

Still referring to FIG. 4, when combine (1) is in operation, bats (3a 1-5) shown in cross-section, will strike the plants. Bat (3a1) is shown having struck a portion of plant (10a) whereupon one or more capsules (12) may be torn off and/or some of the seed (14a) may be released and may fall on the ground. Seed released in this way will not be recovered by the header (2) unless the momentum of the reel sweeps some of the seed (14b) which is released by impact of bat (3a1) on plant (10a) into the header (2). As reel (3) continues to rotate in direction (5), bat (3a1) will contact plant (10b) and bend it away from header (2) before bat (3a5) or another bat comes around and pulls plant (10b) toward the header, as illustrated with bat (3a2) and plant (10c).

As the stem (11) reaches the header, cutter bar (4) cuts the plant and the remaining material is swept into the combine.

FIG. 5 illustrates the advantages that the pygmy non-dehiscent sesame of the present invention provides with respect to mechanical harvesting. Plant (10d) is not pushed away or bent down by bat (3a1) and thus there is no seed similarly positioned to seed (14a) in FIG. 4. The incidence of capsule tear-off is greatly reduced and any seed that does separate from the capsules upon contact between bat (3a1) and plants (10) will be in a position such as seed (14c) which will be swept into the header by momentum. Therefore, the pygmy non-dehiscent sesame provides an advantage in reduction of seed loss during mechanical harvesting.

Because the pygmy lines made according to the method disclosed herein are shorter than typical commercial lines of sesame suitable for mechanical harvesting, pygmy sesame lines do not bridge over the auger of the combine as do the taller varieties. Even though taller branched varieties usually flow through the combine auger better than single stem taller varieties, pygmy sesame lines still present an advantage over even branched taller varieties because pygmy sesame lines can be planted in higher populations in terms of plants per meter and in closer row spacing resulting in more plants per square meter. The auger of the combine can easily handle a high population of single stem pygmy varieties.

The height of the first capsule is measured from the ground to the bottom of the lowest capsule on the main stem. With modern combines, for all sesame varieties, 15 cm is an acceptable value for the height of the first capsule in level fields, while the optimum height is 30 cm. As shown in FIG. 1, the original pygmy sesame used in the breeding method disclosed herein exhibited a height of first capsule below 15 cm, which was below the minimum height for the typical modern combine. However, progeny fell in between the minimum of 15 cm and the optimum of 30 cm. It is preferable, to plant a pygmy variety made according to the invention in a fairly level fields to enable standard combines to capture all of the capsules (and enclosed seed) into the combine. By utilizing level fields, the height of first capsule will be fairly consistent and the combine can be set at a level to maximize capture of plants with capsules at the appropriate level.

The shorter height of the pygmy sesame line of the invention further provides the additional advantages of lodging resistance and the ability to plant higher populations in a given area than would be possible with taller plants.

The amount of lodging is highly correlated to the amount of wind resistance. Taller plants present more resistance to the wind, and thus there is more torque on the base of the plant. When excessive torque is applied, the plants may break over. Pygmies present less resistance to the wind than taller varieties. In addition, the wind speed diminishes closer to the ground, and thus there is less force hitting pygmy sesame as compared to taller varieties.

Pygmies are advantageous for high population sesame planting methods. Pygmies are advantageously employed in a method of agriculture comprising increasing the number of sesame plants per linear foot in a planting row. Pygmies are also advantageously employed in a method for employing closer row spacing in a sesame field planting resulting in more plants per square meter.

Close row spacing is advantageous because the plants provide a canopy more rapidly, thereby inhibiting weed growth. Weeds are "shaded out" by a canopy because weeds sprouting from the ground under the canopy die or are stunted from the lack of sunlight. By planting in closer row spacing, the farmer has lower inputs (e.g. lower resources that are used in farm production, such as chemicals, equipment, feed, seed, and energy) since he does not have to cultivate (weed). Pygmy sesame planted in 15 to 20 cm rows can be used in a method of sesame agriculture which omits the step of cultivation. Omitting the cultivation is advantageous in that it reduces the growing costs since cultivation requires fuel (diesel), operator hours, and maintenance.

The pygmy sesame line of the invention can thrive with more plants per linear meter and make the practice of overplanting more productive. Farmers generally engage in the practice of overplanting in order to ensure the maximum production of their acreage. If normal height sesame is planted, and the overplanting results in more than 10 plants per linear meter, some plants will shade out others. The shaded plants either die out, resulting in self-thinning, or survive as "minor plants" as defined in Langham, D. R. 2007. "Phenology of sesame," In: J. Janick and A. Whipkey (ed.), Issues in New Crops and New Uses, ASHS Press, Alexandria, Va. The minor plants do not produce a commensurate amount of seed for the moisture and nutrients that the minor plants use. In contrast, when pygmy sesame according to the invention is overplanted, less shading occurs with a high population within a row. The minor plants are more productive In high population normal height sesame planting, plants may compete for light, leading to a release of auxins that make the plants grow faster. This faster growth may result in taller plants which may also have thinner, weaker stems. Increased height and stem thinness may make the plant more susceptible to lodging. Heretofore known varieties of sesame throughout the world could not be planted in high population or close row spacing because of the associated increase in the susceptibility to lodging resulting therefrom.

Pygmy sesame has a higher harvest index than taller sesame varieties. The harvest index is the ratio of weight of the seed to the weight of the entire plant including seed. Since there is a set amount of moisture and fertility available to any crop in a given field, it is generally more advantageous for a plant to use those resources to produce seed than to use the resources to make the vegetative parts of the plant such as leaves, stems, and capsules. While there must be a balance (since the vegetative parts are necessary to the plant to capture sun and conduct photosynthesis to generate energy which is used to make seed), seed is the reason that sesame crops are planted.

A second advantage of high harvest index is that most modern combines are designed to clean grain that has a low proportion of dockage and foreign matter to seed. The higher the harvest index, the cleaner the sesame will be which exits the combine. This reduces cleaning and trucking costs.

Pygmy sesame is advantageous as a crop since the high population planting reduces the number of weeds that plague crops of taller varieties of sesame.

One of the more difficult parts of raising mechanized sesame is weed management. With manual methods of raising sesame, manual labor was employed to remove weeds by hand, but in modern mechanized agriculture, weed management employs mechanical operations and/or herbicides.

Mechanical operations include disking and harrowing prior to planting to eliminate all the weeds in the field and then cultivating (breaking up the surface soil around the plants with a farm implement called a cultivator in order to destroy weeds) after the crop gets to a sufficient height. However, it is difficult to cultivate sesame because it develops slowly in the first 30 days while it is putting its root down (Langham, D. R. 2007. "Phenology of sesame," In: J. Janick and A. Whipkey (ed.), *Issues in New Crops and New Uses*, ASHS Press, Alexandria, Va.). It takes almost 20 days before a cultivator can be used in a sesame field without damaging the sesame.

In addition to mechanical means, pre-emergence herbicides may be used which are applied after planting and before the sesame seedlings emerge from the ground. These herbicides provide 30-40 days of protection from most weeds. Sesame is primarily a rotation crop for cotton, corn, and soybeans. Such crops may rely on the use of glyphosate to kill all weeds except the crop. The plants are genetically modified organisms (GMO) in that the gene that protects these crops from the glyphosate is inserted into the germplasm. Although no GMO sesame is known, producing a glyphosate resistant sesame would not provide a solution to the weed problem because as a rotation crop for cotton, corn, and soybeans a glyphosate-resistant sesame would be an undesired plant ("weed") in those crops, which would be unacceptable to the farmers. Further, some countries to which sesame is marketed do not permit GMO corps.

Another method of weed control relies upon the growth of the plants in the adjoining rows. As the plants grow, the respective leafs from plants in adjoining rows will be relied upon to prevent new weeds in the space between the rows from getting sunlight (e.g. "shade out" the weeds). The adjoining rows are said to "close in." However, this may take an additional 20-50 days before the area between the rows is shaded out. The time required is influenced by the variety of the sesame (height of the plant and branching) and the spacing between rows. Standard row spacing for sesame (75 to 100 cm) favors taller varieties for shading out which generally have more branching as well.

It has now been found that pygmy sesame (py/py) can be used in a method for close row planting wherein the rows are about 20 to 40 cm apart and provide for rapid closing up. Planting at 20 cm (the row spacing used for wheat but heretofore not employed for sesame), the rows close in within 20 days, thereby shading out weeds between rows. Not having a suitable over the top herbicide (e.g., an herbicide that can be sprayed on the field and kill the weeds not the sesame plants) for sesame, the faster the crop can close up and shade out weeds, the better.

Advantages of Improved Non-Dehiscent Pygmy: Geographical Distribution

Currently sesame is primarily grown as a rotation crop on farms that grow cotton, sorghum, peanuts, sunflowers and soybeans. Farmers of these crops usually have row equipment for these crops which allows for row spacing of 50 to 100 cm, usually 75 to 100 cm. The equipment includes row planters and cultivators. The existing farm equipment works well for planting standard height sesame as it will close up between rows to address weeds which would otherwise be harmful to the crop.

However, in areas in which the primary crop is wheat, farmers possess row equipment (drills) for planting in 15 to 20 cm rows and likely do not have cultivators. While some drill equipment may be modified by the farmer for wider row spacing, other drills cannot. Even if the equipment can be modified, such farmers are still limited to planting sesame in fields that are clean of weeds in the absence of a cultivator.

Pygmy sesame may be used in a method of close row planting, thus allowing farmers to use drill equipment adapted to planting in 15 to 20 cm rows. This will allow expansion of sesame growth to areas in which the equipment for standard row of 75 to 100 cm are rare.

Advantages of Improved Non-Dehiscent Pygmy: Lower Inputs

Pygmy sesame planted in 15 to 20 cm rows can be used in a method of sesame agriculture which omits the step of cultivation (weeding). Omitting the cultivation is advantageous in that it reduces the growing costs since cultivation requires fuel (diesel), operator hours, and maintenance.

Pygmy sesame can be used in a method of sesame agriculture employing increasing the speed of combining crops by employing pygmy sesame having a high harvest index. The combines can move through the field faster because there is less plant matter going through the combine. Generally, the price charged by custom operators for combining is based on amount of time required. Therefore, reducing the time required reduces the cost of combining. Pygmy sesame can be used in a method of sesame agriculture in which sesame is grown under low moisture conditions and/or low fertility conditions. Since pygmy lines will produce more seed per unit of moisture/fertility than non-pygmy lines, pygmy lines are suitable for use in such a method.

The following paragraphs provide further details about the characteristics of the pygmy sesame of the invention.

Sesame plants have been studied for their response to seasonal and climatic changes and the environment in which they live during the different phases and stages of growth and development. This type of study, called "phenology", has been documented by the inventor in Langham, 2007, supra, ¶49.

Table I summarizes the phases and stages of sesame, and will be useful in describing the present invention.

TABLE I

Phases and stages of sesame.

| Stage/Phase | Abbrev | End point of stage | DAP$^z$ | No. weeks |
|---|---|---|---|---|
| Vegetative | VG | | | |
| Germination | GR | Emergence | 0-5 | 1− |
| Seedling | SD | 3$^{rd}$ pair true leaf length = 2$^{nd}$ | 6-25 | 3− |
| Juvenile | JV | First buds | 26-37 | 1+ |
| Pre-reproductive | PP | 50% open flowers | 38-44 | 1− |
| Reproductive | RP | | | |
| Early bloom | EB | 5 node pairs of capsules | 45-52 | 1 |
| Mid bloom | MB | Branches/minor plants stop flowering | 53-81 | 4 |
| Late bloom | LB | 90% of plants with no open flowers | 82-90 | 1+ |
| Ripening | RI | Physiological maturity (PM) | 91-106 | 2+ |
| Drying | DR | | | |
| Full maturity | FM | All seed mature | 107-112 | 1− |
| Initial drydown | ID | 1$^{st}$ dry capsules | 113-126 | 2 |
| Late drydown | LD | Full drydown | 127-146 | 3 |

$^z$ DAP = days after planting. These numbers are based on S26 in 2004 Uvalde, Texas, under irrigation.

Dwarf lines are identified by having a low plant height, short internodes, and high capsule density with a resulting high harvest index. Most dwarf lines had triple capsules per leaf axil, but dwarf lines can have a single capsule per leaf axil. The latter lines have a shorter internode length than the triple capsules still conveying the image of high capsule density. In the world germplasm there are short lines that do not have short internodes, have few capsules, and have little yield. These lines are not considered to be dwarves.

In order to breed a shorter sesame line, a sesame dwarf plant may be used in the breeding method. A preferred dwarf is one that has a gene which, when crossed, will exhibit as many as 25% short plants in the F2, indicating a recessive py/py gene. A suitable sesame dwarf is K28p which may be used in a breeding method to provide characteristics of pygmy because the py/py gene is recessive creating more short plants in the F2 generation. An ND or IND sesame line should also be used in the breeding method.

Table II summarizes the paragraphs above using the following designators: T=tall normal plants with no dwarf or pygmy genes, P=pure pygmy, and D=pure dwarf genes.

TABLE II

Height of plant crossing results based on types of parents

| Parents | F1 | F2 | Comments |
|---|---|---|---|
| T and P | T | T and P | Usually in the F2 there are less than 5 to 20% P and the rest T with no observed intermediate heights. The py/py allele is recessive and the expected ratio would be 25% py/py. However, the same gene that shortens the internode lengths, shortens the hypocotyl of the seedling, which in turn reduces the probability of emerging above the surface of the soil after germinating. The germination rates are around 5% when planted deep in compacted soils, and around 20% when planted shallow in light soils. In the F3 and subsequent generations, the P will be pure P. Some of the T will segregate 5-20% P, while some of the T will be pure T, and the latter will be pure T in subsequent generations. |
| T and D | T | T and D | Usually in the F2 there is a range of plant heights between the two parents. There will be less than 5% plants that are as short as the D, and no plants that are shorter than the D parent. In the F3 the T will generally be T, the D will generally by D, while the intermediates will go in both directions. |
| D and P | D | D and P | Usually in the F2 there are less than 5 to 20% P and the rest D with no intermediate heights. In the F3 and subsequent generations, the P will be pure P. Some of the D will segregate 4-20% P, while some of the D will be pure D, and the latter will be pure D in subsequent generations. |
| P and P | P | P | From the F1 on, all of the progeny are P. |
| T and T | T | T | From the F1 on, all of the progeny are T. There is heterosis in sesame and in the F1 many progeny will be taller than either parent, but in subsequent generations the majority of the selections will be between the heights of the two parents. There can also be be selections that are taller and selections that are shorter than either parent. |

In creating pygmy IND lines, Table II explains the probabilities facing the breeder in developing a P, while Table III below summarizes the probabilities of getting ND and IND using the following symbols: X=shattering, C=close to ND, N=ND, and I=improved ND.

TABLE III

Shatter resistance crossing results based on types of parents

| Parents[z] | F1 | F2 | Comments |
|---|---|---|---|
| X and N | X | X, C, and N<br>Most X | Usually in the F2 there are less than 2% N and often zero N. Selecting C will also rarely end up segregating N. It is preferred to perform enough crosses and plant out as many F2 plants as feasible and only select N plants. |
| X and I | X | X, C, N, and I<br>Most X | Same as above |
| C and N | C | X, C, and N<br>Most C | X are rare and although it is preferred to select N plants, there are many C plants with good commercial characters that have the potential to segregate N. |
| C and I | C | X, C, N, and I<br>Most C | Same as above |
| N and N | X, C, and N | X, C, N, and I<br>Most N | X and C are rare but the characters that produce N can fall apart. Although I are rare, the first I were a result of N and N crosses. |
| N and I | X, C, N, and I | X, C, N, and I<br>Most N | X and C are rare. Higher probability of getting I than above. |
| I and I | X, C, N, and I | X, C, N, and I<br>Most I | X and C are rare. Highest probability of getting I, but there are many N |

[z] There is no reason to make a cross where one of the parents is not an "N" or "I"

Prior to the method disclosed herein, all known shatter resistant sesame parents were tall ND (TN) or tall IND (TI). All potential pygmy parents where pygmy shattering (PX). Genetically, there is no difference in using the pygmy as a male or female, i.e., PN and PI can be achieved with either parent as a female. Pragmatically, it is better to use the TN/TI parent as the female. A capsule produced by a cross will have the characteristics of the female plant. Thus, the capsule(s) will be N/I and the seed will not shatter out as the capsule dries down. It is preferable to use a TI over a TN. Shatter resistance is produced by multiple genes and TI lines have more of the appropriate genes. Table IV shows the flow of selections by crossing a PX male by a TI female.

TABLE IV

Results of crossing a tall IND line by a pygmy shattering line

| Generation | Plant/ Pygmy | Comments |
|---|---|---|
| Cross | TI | The crossed plant and capsules have the characters of the female. |
| F1 | TX | T and X characters are dominant over P and I. |
| F2 | TX | The majority of the progeny will be TX, and these should not be carried forward |
|  | PI | A PI plant should be selected. In 100 progeny, the probability is against a single PI plant, and thus 300-1,000 progeny plants should be planted from each F1 plant. It is preferred to achieve PI plants by performing dozens of crosses between TI and PX lines and planting about 300 progeny from each cross in the F2. Using this methodology, one will obtain multiple PI plants with different genetic backgrounds. |
|  | PN/PC | There is a greater probability of finding a PN plant than a PI plant and an even greater probability of finding a PC plant. PN plants are selected to carry further if there are too few PI selections. The same with PC. |
|  | PX | Of the pygmies from this cross, the highest probability is PX, but these are only carried further if there are no PI/PN/PC selections. |
|  | TI/TN/TC | Each of these selections has the potential to segregate into a PI/PN, but these are usually only taken if there are no pygmy selections. |
| F3 and beyond | PI | There are many genes involved in ND and IND. A PI F2 may segregate to more or less shatter resistance. The pygmy character is stable and will be pure from the F2 on. Finding a PI is the first step of developing a commercially acceptable PI variety. As discussed below, other characters should preferably be introduced into the line to result in an acceptable yield and biotic and abiotic resistances. |
|  | PN/PC | Any PI found in these selections are normally selected and carried forward. PN plants with good agronomic characters may be carried forward, but the probability of a PC segregating to a PN/PI after the F3 generation is low, and thus no PC plants are selected to carry further. |
|  | TI/TN/TC | Theoretically, one third of these F2 selections will be pure T. The other two thirds can segregated PI/PN and are carried forward. |

Once a PI line is found, the PI plants should be used as the male parent instead of the PX lines.

In an example of the method of the invention, D54p was crossed against many TI lines. This aggregated desirable characters by using building blocks. Sixty-two PN and fifty PI (for a total on 112 lines) have been developed based on this methodology. Although the preference is PI, there are PN lines with higher yield in some environments. Therefore, both PN and PI lines may become varieties.

In order to become a commercial variety, the line should exhibit comparable yield to existing varieties. The following tables show the progenitor K28p, three varieties (S25, S26, and S27) and three progeny (D51p with its genealogy depicted in FIG. 6; D50p with its genealogy depicted in FIGS. 7; and D54p with its genealogy depicted in FIG. 8). Table V shows the characters that determine potential yield. There are some characters presented that are neutral, but are presented because they affect the other characters.

TABLE V

Characters that determine potential yield

| Character | | | | | | | |
|---|---|---|---|---|---|---|---|
| Pygmy alleles (Character 1) | K28p py/py | S25 PY/PY | D51p py/py | S26 PY/PY | D50p py/py | S27 PY/PY | D54p py/py |

The pygmy allele is recessive with the py/py being homozygous pygmy and PY/PY being homozygous normal.
In the homozygous pygmy state, the plant height, height of first capsule, and internode length are shortened as shown below.

| Branching style (Character 2) | K28p U | S25 B | D51p U | S26 B | D50p B | S27 B | D54p U |
|---|---|---|---|---|---|---|---|

The potential amount of true branching in a line. Subjective rating based on the following values:
U = Uniculm - no branching except weak branches in open
B = True branches
U.S. Pat. No. 6,781,031 provides more detail as to the definition of "true branches"
As shown above, there are uniculm and branched pygmies. In some pygmy lines there are branches that are not expressed. In order for a branch to develop, sunlight needs to hit the growing tip in the leaf axil. With shorter internodes, the sunlight does not penetrate the canopy to enable the branches to develop. There are pygmies such as D50p above with slightly longer internodes that will branch.
Branching is not as important for pygmies because they are capable of being planted in high populations where branches do not contribute a significant amount to the yield.

| Number of capsules per leaf axil (Character 3) | K28p 3 | S25 1 | D51p 1 | S26 1 | D50p 1 | S27 1 | D54p 1 |
|---|---|---|---|---|---|---|---|

The predominant number of capsules per leaf axil in the middle half of the capsule zone. Subjective rating based on the following values:
1 = Single
3 = Triple
U.S. Pat. No. 6,781,031 presents more detail as to how to differentiate single capsules per leaf axil from triple capsules per leaf axil. There are single lines that have a few nodes with triple capsules, and triple lines have single capsules at the bottom and top of the plant. A 1998 Sesaco study showed that single capsule lines averaged 0.91 capsules per leaf axil and the triple capsule lines averaged 1.64 which is not quite double. In addition, in a 1999 Sesaco study, the axillary capsules averaged 79.4% seed weight per capsule of the central capsules. Based on source/sync issues, triple capsules do not imply higher yields.
Under the growing conditions most encountered (rainfed crops in low rainfall areas), single capsule lines are preferred. Triple capsule lines are not suitable unless the height of the the first capsule is high enough to permit mechanized harvest.

| Days to physiological maturity (Character 4) | K28p 88 | S25 100 | D51p 99 | S26 106 | D50p 98 | S27 106 | D54p 102 |
|---|---|---|---|---|---|---|---|

The number of days from planting until 50% of the plants reach physiological maturity. The value is based on the average of a minimum of three plots. The values within Sesaco range from 77 to 140 days with an average of 97.
The ripening phase of sesame is from the end of flowering until physiological maturity. Physiological maturity (PM) is defined as the point at which ¾ of the capsules have seed with final color. In most lines, the seed will also have a seed line and tip that are dark. The concept of physiological maturity in sesame was developed by M. L. Kinman (personal communication) based on the concept of determining the optimum time to cut a plant and still harvest 95-99% of the potential yield. When the seed has final color, the seed can germinate under the proper conditions. If the plant is cut at physiological maturity, most of the seed above the ¾ mark will go to final color and are mature enough to germinate, but will not have as much seed weight. Since in even a fully mature plant, there is less seed weight made at the top of the plant, this loss of seed weight does not seriously affect the potential seed weight of the plant
Although present harvest methods let the plants mature and go to complete drydown, PM is important because after that point, the crop is less susceptible to yield loss due to frost or disease. The PM is also important if the crop is to be swathed or harvest aids are to be applied.
The range of PM for pygmy lines is preferably similar to standard height ND or IND current varieties. The presence of pygmy genes will not be a range inhibiting factor in that a comparable PM may be selected.

TABLE V-continued

Characters that determine potential yield

| | | | | | | | |
|---|---|---|---|---|---|---|---|
| Height of Plant (cm) (Character 5) | K28p<br>52 | S25<br>138 | D51p<br>87 | S26<br>153 | D50p<br>84 | S27<br>141 | D54p<br>90 |

The height of the plant from the ground to the top of the highest capsule with viable seed. A minimum of 3 representative plants are measured and averaged. The values within Sesaco range from 52 to 249 cm with an average of 135 cm.

The plant architecture shows the plant height and two other characters discussed below: height of first capsule and capsule zone length. The sum of the two latter characters is the plant height. The plant architecture of the 7 lines is shown in FIG. 1.

K28p is too short and does not have enough yield potential to be commercially viable. The three pygmy progeny are below 100 cm and have sufficient yield to be commercially viable. In the first combine test with D54p, the reel brought the sesame into the cutter bar without pushing the plants forward, and the short plants fell into the header and were easily fed by the auger into the feeder housing of the combine. As long as there is sufficient yield, shorter lines are preferable for mechanical harvest with a combine.

| | | | | | | | |
|---|---|---|---|---|---|---|---|
| Height of first capsule (cm) (Character 6) | K28p<br>9 | S25<br>57 | D51p<br>24 | S26<br>57 | D50p<br>18 | S27<br>45 | D54p<br>24 |

The height of the first capsule from the ground to the bottom of the lowest capsule on the main stem. A minimum of 3 representative plants (the same as are used for height of plant) are measured and averaged. The values within Sesaco range from 20 to 193 cm with an average of 54 cm. As shown in FIG. 1, the original source souce of pygmy was below the minimum height, but the progeny fall in between the minimum of 15 cm and the optimum of 30 cm. This short height of the first capsule dictates that the pygmies be planted in fairly level fields if the combine is to get all of the capsules (and enclosed seed) into the combine bin. However, just as a certain amount of shattering is acceptable as long as there is a good yield, it may be acceptable to leave some capsules (seed) that would be below the cutter bar of the combine. The countours of the field should be considered before planting pygmies.

| | | | | | | | |
|---|---|---|---|---|---|---|---|
| Capsule zone length (cm) (Character 7) | K28p<br>42 | S25<br>81 | D51p<br>63 | S26<br>96 | D50p<br>66 | S27<br>96 | D54p<br>66 |

The capsule zone extends from the bottom of the lower capsule on the main stem to the top of the highest capsule with viable seed on the main stem. The data is derived by subtracting the height of the first capsule from the height of the plant. A minimum of 3 representative plants (the same as are used for height of plant) are measured and averaged. The values within Sesaco range from 18 to 188 cm with an average of 81 cm. Technically, the capsule zone should include the capsule zones on all of the branches. However, when mechanically planting without any manual thinning, the populations vary considerable. In low populations the plant will have many branches, and in high populations the plant may have no branches. In comparing lines across fields, environments, and years, the capsule zone length of the main stem can be used effectively to select progeny to carry forward.

Since the capsule zone contains the plant production, on initial examination of the figures above, it would seem that the pygmy necessarily has less yield than the normal lines. However, as shown below with the number of node pairs and the internode length, pygmies have the same potential yield.

| | | | | | | | |
|---|---|---|---|---|---|---|---|
| Number of node pairs (Character 8) | K28p<br>16 | S25<br>29 | D51p<br>28 | S26<br>27 | D50p<br>25 | S27<br>32 | D54p<br>31 |

The number of capsule node pairs from the lowest capsule node to the highest node with capsules with viable seed on the main stem of the plant. A minimum of 3 representative plants (the same as are used for height of plant) are measured and averaged. The values within Sesaco range from 10 to 54 node pairs with an average of 25.

The count is made after the plants stop flowering. On opposite and alternate arranged leaves, each pair of leaves is counted as one node pair. In some lines, there are three leaves per node for at least part of the plant, and those are counted as one node pair. In some plants, flowers may not have produced capsules on one or more the leaf axils in a node. These node pairs should still be counted. This is not a capsule count; it is intended to denote the number of node pairs that the plant tried to set capsules.

Triple capsule lines generally have fewer node pairs. In comparing lines, the value is compared to the other lines with the same branching style and number of capsules per leaf axil.

TABLE V-continued

Characters that determine potential yield

Figure 9:
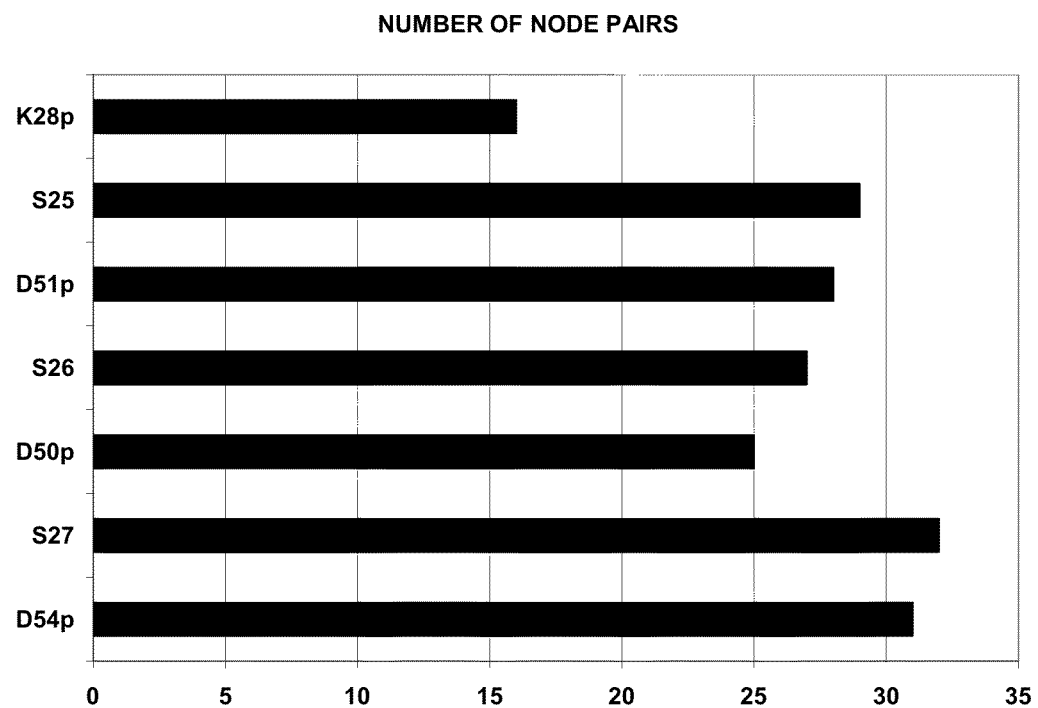
FIG. 9 depicts the number of node pairs of the seven lines.
Figure 10:
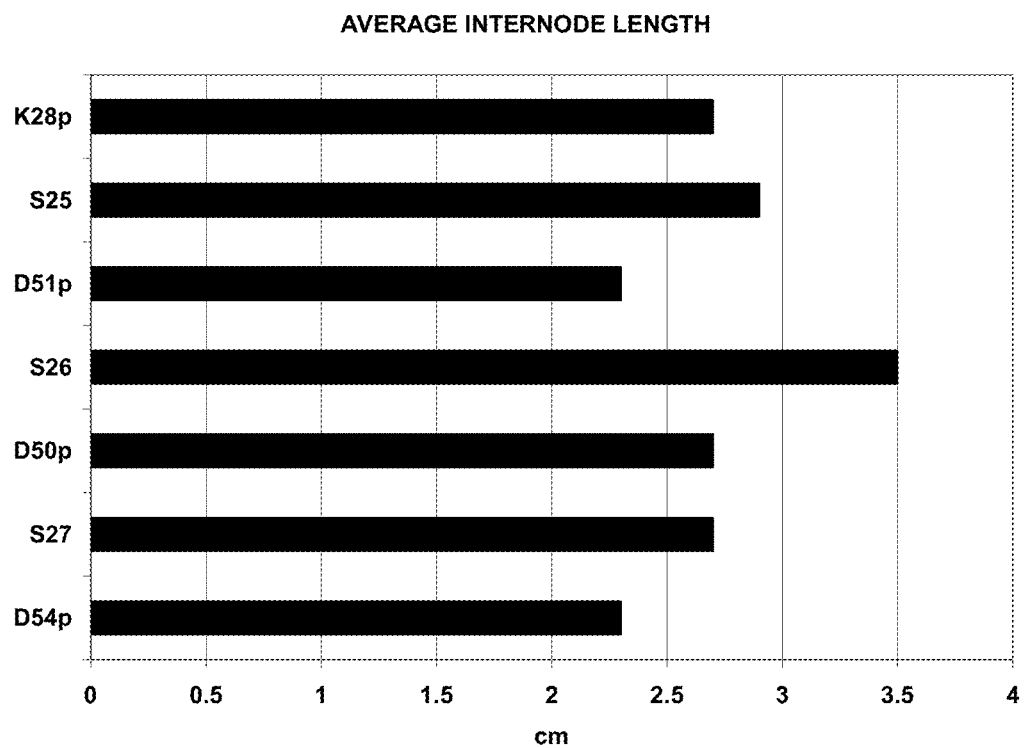
FIG. 10 depicts the average internode length of the seven lines.
Figure 11:
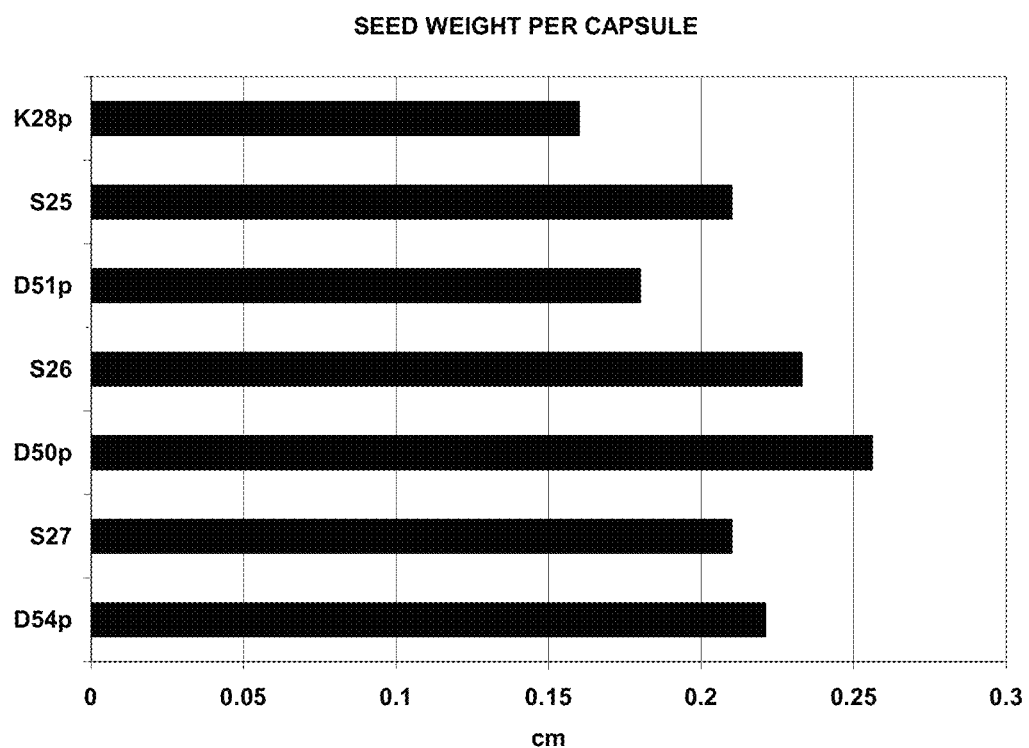
FIG. 11 depicts the seed weight per capsule of the seven lines.
Figure 12:
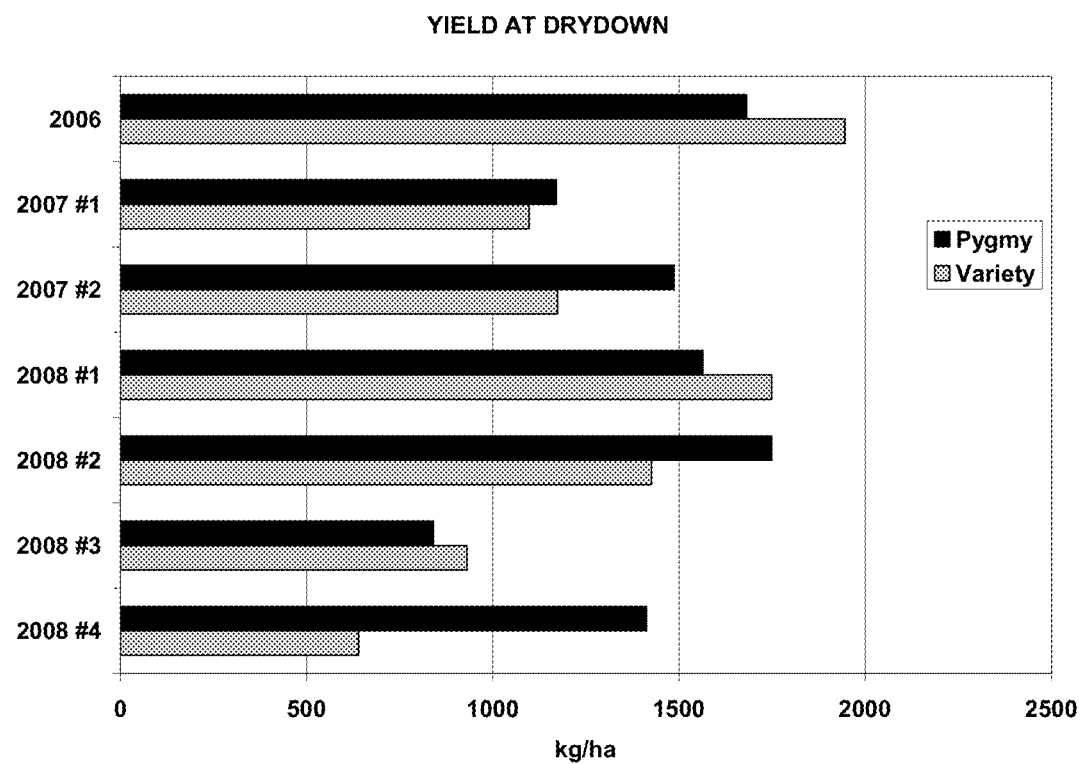
FIG. 12 depicts a comparison of yields of the varieties and pygmy lines in various environments.

|  | | | | | | | |
|---|---|---|---|---|---|---|---|
| | In years when the amount of moisture available to the plant is irregular, node pairs can become very irregular, particularly on triple capsule lines. In the upper portions of the plant, it may become easier to count the capsule clusters and divide by 2. While it is possible to count node pairs after leaves have fallen, it is much easier to count while the leaves are still on the plant. FIG. 9 compares the number of node pairs of the seven lines. The progenitor K28p has fewer node pairs, but as can be seen above, pygmy progeny was selected that had similar number of node pairs to the normal parent. There are pygmy lines with more node pairs than either parent. | | | | | | |
| Average internode length within capsule zone (cm) (Character 9) | K28p 2.7 | S25 2.9 | D51p 2.3 | S26 3.5 | D50p 2.7 | S27 2.7 | D54p 2.3 |
| | The average within the capsule zone. The same representative plants used above are used for this data. The height of the plant, the height of the first capsule, and the number of nodes are used for the following formula: height of plant subtracted by height of the first capsule and then divided by the number of node pairs on the main stem. Within Sesaco the range is between 1.09 and 8.09 cm with an average of 3.35 cm. The internodes at the bottom of the capsule zone are longer than the internodes at the top of the plant. Generally, triple capsule per leaf axil lines have longer internodes than single capsule lines. In triple capsule lines the axillary capsules should be as tight to the stem as possible in order to avoid rubbing off the plants in the wind, By being tight, the intenodes need to be almost of long as the capsule. Normally a stem has 4 sides and the central capsules rotate 90 degrees from the central capsules in the node below. Thus, in a few lines there can be an exception where the central capsules tuck in between the axillary capsules above and the internode length is shorter than the capsule length. Triple capsule lines generally have longer internode lengths because there needs to be room on the stem to place the extra capsules. There are triple capsule lines that can have shorter internode lengths by either having shorter capsules (less seed) or by angling the axillary capsules away from the stem (easy to break off capsule in plants rubbing in the wind). The shorter internode character by itself is not a definitive pygmy identifier. As can be seen above there is some overlap between normals and pygmies. FIG. 10 compares the internode lengths. Pygmies are shorter and have a lower height of the first capsule than normal lines because of the short internode length. It is also this short internode that allows the pygmies to have a sufficient number of node pairs without increasing the plant height. Aside from keeping the plants shorter, the internode length has another implication: the leaves end up shielding the leaf axil from sunlight. As stated in Langham (supra), in order to form a branch sunlight needs to reach the leaf axil. There are pygmy lines that have branching genes that will rarely branch, and yet when they are crossed against a non-branched normal, in the F1 they have branches indicating that the pygmy had branching genes. These lines have a branching genotype and a uniculm phenotype. When a pygmy such as D50p has longer internodes, then there can be branching. | | | | | | |
| Seed weight per capsule (SWC) (g) (Character 10) | K28p 0.160 | S25 0.213 | D51p 0.183 | S26 0.233 | D50p 0.256 | S27 0.210 | D54p 0.221 |
| | The weight of the seed in a capsule from the center of the capsule zone. The value is based on the average of a minimum of three samples. After the plants are physiologically mature, two capsules are taken from five plants from the middle of the capsule zone. On three capsule per leaf axil lines, one central capsule and one axillary capsule should be taken from the same leaf axil. This test is known as the 10cap test and several measures are derived from this test. The capsules are dried out to insure the seed is dry, and then the seed is threshed out of the capsules and weighed. The total weight is divided by ten to get the seed weight per capsule. The capsules can be sampled from physiological maturity through complete drydown without an effect on this character. After drydown, only capsules with all their seed are taken. Thus, this test cannot be done on shattering lines after drydown. Within Sesaco the range is between 0.053 and 0.476 g with an average of 0.221 g. Generally, the capsules in the middle of the capsule zone have the highest SWC on the plant. Generally, triple capsule lines have a lower SWC than single capsule lines. The axillary capsules have less less SWC and in a triple capsule line, and half of the capsules in each sample are axillary capsules. When the pygmies were first discovered, it was feared that SWC might be a limiting factor in yield. However, as shown in FIG. 11, there are pygmy lines that have comparable SWC to the present varieties. Being a triple capsule line, the progenitor K28p has a very low SWC. The presence of pygmy genes will not be a yield inhibiting factor in that a comparable SWC may be selected. | | | | | | |

TABLE V-continued

| Characters that determine potential yield | | | | | | | |
|---|---|---|---|---|---|---|---|
| Non-leaf harvest index (%) (Character 11) | K28p NT (not tested) | S25 31.7 | D51p NT | S26 29.6 | D50p NT | S27 28.2 | D54p 36.7 |

The ratio of seed to the whole plant without leaves. The data is derived by dividing the seed weight of a plant by the weight of the stems, capsules, seed, and leaves and converting it to a percentage. It is time consuming to take the data and it is not taken often, and thus Sesaco does not maintain ranges and averages of the values.

A true harvest index measures the weight of the leaves as part of weight of the total plant. Sesame presents a unique problem in measuring harvest index because it self-defoliates. The leaves begin to fall before the seed at the top of the plant has filled. If the plant is cut, dried, and weighed while the leaves are still on the plant, then there is less seed weight. If the plant is cut, dried, and weighed after the top seed has filled, there is less plant weight because the leaves have fallen off. Generally, triple capsule lines have higher non-leaf harvest indices than single capsule lines. It is misleading to compare single to triple lines because the leaves are not counted. Triple capsule lines necessarily have larger leaves to produce enough seed in the 3 capsules in the leaf axil.

Non-leaf harvest indices are still very time consuming and have only been done three times by Sesaco. It was found that the index varies considerably with the environment. In years when there is more rain and yields are higher, the harvest index is higher than in dry years.

In the limited testing that has been done, the pygmies have had higher non-leaf harvest indices than the normal lines. However, it is logical that in the future the ranges of the two will overlap.

| Seed weight - 100 seeds from 10 cap test (g) (Character 12) | K28p 0.255 | S25 0.304 | D51p 0.270 | S26 0.330 | D50p 0.350 | S27 0.314 | D54p 0.326 |

The weight of 100 seeds taken from the 10cap tests which are taken from the middle of the plant. The value is based on the average of a minimum of three samples. The 10cap procedures are described under Seed Weight per Capsule (Character No. 10). Once the seed is threshed out of the capsules, 100 representative seeds are counted out and weighed. The seed must be dry. Within Sesaco the range is from 0.200 to 0.455 g with an average of 0.298 g.

The seed weight in the middle of the stem zone is the heaviest seed on the plant. Generally, triple capsule lines have lower hundred weight than single capsule lines. The seed in the axillary capsules is smaller than the seed in the central capsules. The seed from any whole plant is lower that the seed from the 10cap test because the seed in the tips of the capsules is smaller, the seed in the branches is smaller, the seed at the top of the plant is smaller, and although close in size, most of the seed at the bottom of the plant is smaller. This hundred seed weight from the 10cap test is used because it is simple to take and more important, there is a high direct correlation between the weight 100 seeds from the middle of the plant and the weight of 100 seeds from the whole plant. This value is used to compare lines grown under the same conditions and cannot be considered to be the weight of the line under all conditions. The same seed planted in many environments can have a much as a 94% difference using the lowest as a base or 52% difference using the highest sample as a base. Simply said, in some lines the seed can be close to twice the weight under differing conditions.

Pygmies can all produce both small and large seed. The presence of pygmy genes will not be a market inhibiting factor in that a comparable hundred seed weight may be selected.

| Seed color The color of the seed coat (Character 13) | K28p BF | S25 BF | D51p BF | S26 BF | D50p BF | S27 BF | D54p BF |

Subjective rating based on the following values:
WH = White
BF = Buff
TN = Tan
LBR = Light brown
GO = Gold
LGR = Light gray
GR = Gray
BR = Brown
RBR = Reddish brown
BL = Black Seed coat color is taken on mature seeds. If there is any abnormal termination, the colors are not quite as even. The color of immature seed varies. Usually light seeded lines have tan to light brown immature seed; tan, light brown, gold, brown light gray, and gray lines have lighter immature seed; black lines can have tan, brown, or gray immature seed. The majority of the market uses light seed. There are no problems with having light and black color seed on pygmy lines.

Table VI compares Yield at drydown for ND/IND varieties with that of pygmies. This value is taken after the plants are dry standing in the field without cutting and shocking. As a result of winds and rains, the yields in shattering lines are 50 to 100% less than the amount of potential yield if the plants are cut when they are green and all seed that shatters out in the drying process is maintained. Thus there is no yield data for the shattering lines K28p, D51p and D50p. Table VI shows the highest yield in seven nurseries comparing the best variety and the best pygmy line. Within each nursery, the lines were grown in comparable conditions.

TABLE VI

Yield of varieties and pygmies

| | ND/IND Variety | Pygmy | Nursery |
|---|---|---|---|
| Yield at drydown (kg/ha) (Character 14) | 1,945 | 1,682 | 2006 Uvalde, TX. Irrigated, good fertility. |
| | 1,098 | 1,170 | 2007 Uvalde, TX. Irrigated, low fertility. |
| | 1,174 | 1,564 | 2007 Lorenzo, TX. Irrigated, low fertility. |
| | 1,749 | 1,487 | 2008 Uvalde, TX. Irrigated, good fertility. |
| | 1,426 | 1,749 | 2008 Uvalde, TX. Semi-irrigated, good fertility. |
| | 639 | 1,413 | 2008 Lorenzo, TX. Rainfed, low fertility. |
| | An extrapolation of the yield of a field by taking sample yields. On 3 replicated plots, when the plants are dry enough for direct harvest, cut a minimum of 1/5000 of a hectare (Sesaco uses 1/2620) in the plot and place the plants in a cloth bag. Thresh the sample in a plot thresher and weigh the seed. Multiply the weight by the appropriate multiplier based on area taken to provide the extrapolated yield in kg/ha. Under good moisture and fertility the standard height ND/IND varieties have exhibited higher yields when planted at 76 and 100 cm row spacing than pygmy lines. However, when there are limits to the moisture or fertility, the pygmies have higher yields than the non-pygmy varieties and are thus an option for a method of sesame agriculture under low moisture and/or fertility conditions. | | |

Table VII discusses factors that influence an ideal yield of a sesame crop (drought, diseases, pests, and lodging prior to flower termination) or reduce the ideal yield (shatter resistance, lodging after flower termination, and dry pods on a green plant). Shatter resistance is the character that allows sesame to be left in the field to dry and then harvested with a combine.

TABLE VI

Characters that Influence potential yield

| | K28p | S25 | D51p | S26 | D50p | S27 | D54p |
|---|---|---|---|---|---|---|---|
| Shaker shatter resistance (%) (Character 15) | 2.2 | 70.8 | 14.8 | 73.0 | 6.3 | 72.8 | 77.4 |
| The amount of seed retention after the capsules are dry, inverted, and put through a shaker. The data is derived from 10cap testing as described in the Seed Weight per Capsule (Character No. 10). The capsules should be dried and inverted. The capsules and any seed that has fallen out should then be placed in flasks on a reciprocal shaker with a 3.8 cm stroke with 250 strokes/min for 10 minutes (see U.S. Pat. No. 6,100,452). The seed that comes out of the capsules should be weighed as 'out seed.' The retained seed should be threshed out of the capsules and weighed to compute the 'total seed'. The shaker shatter resistance (SSR) is computed as a percentage as follows: (total seed − out seed)/total seed. The capsules can be sampled from physiological maturity through complete drydown without an effect on this character. After drydown, only capsules with all their seed are taken. Within Sesaco the values range from 0 to 100% with an average of 56%. After the initial studies in the development of this rating, the 10cap testing is only done on lines that are showing visual shatter resistance and are candidates for a variety. As a result, the average continues to climb over time.<br>SSR is the most important piece of data to determine whether a line has the potential to develop into a variety. Preferably, this threshold is at least 65%, and more preferred is a threshold of 70%. A character of IND (improved non-dehiscence - Character No. 18) explained below is most preferred.<br>In U.S. Pat. No. 6,100,452 the original sources of ND were identified along with the six characters that were joined to enable ND. Once a line is ND, then that line is used as a parent to pass ND to shattering lines. While it is necessary to use an ND sesame in a breeding method to produce progeny with the ND characteristic, it may be necessary to make multiple crosses before sucesss is achieved.. ||||||||

TABLE VI-continued

Characters that Influence potential yield

Figure 13:
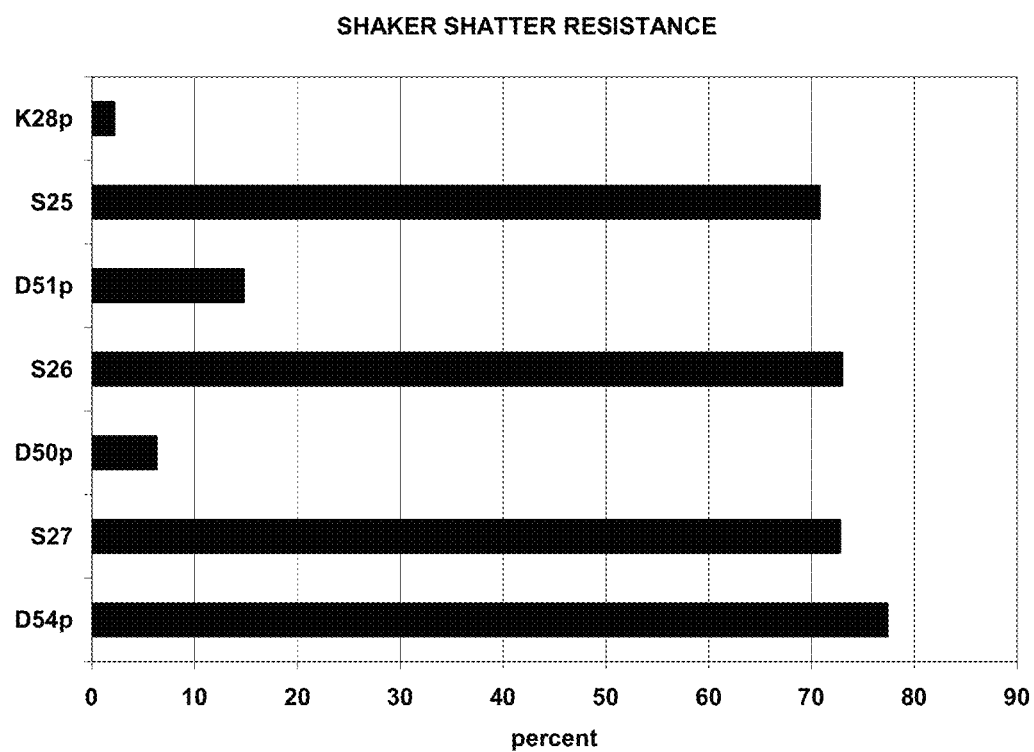
FIG. 13 depicts the shaker shatter resistance of the seven lines.

| | | | | | | | |
|---|---|---|---|---|---|---|---|
| | FIG. 13 compares seven sesame lines. D54p is exemplary of a suitable pygmy line. D54p exhibits both pygmy and ND characters. Both characters are necessary for the pygmy lines that can be harvested mechanically.<br>There is a very low probability of success in crossing a shattering line against lines with ND, because there are six capsule characters that must be modified. It is disclosed herein that a preferred method of breeding includes passing the pygmy genes from an ND pygmy to an ND normal as compared with crossing a shattering pygmy with an ND normal. | | | | | | |
| Non-dehiscent test (Character 16) | K28p<br>XX | S25<br>ND | D51p<br>XX | S26<br>ND | D50p<br>XX | S27<br>ND | D54p<br>ND |
| | A line that has passed the non-dehiscent test of having shaker shatter resistance >64.9% is considered an ND line in accordance with U.S. Pat. No. 6,100,452.<br>The values used are:<br>ND = Non-dehiscent line<br>XX = Line that does not pass the non-dehiscent test<br>Lines are designated as ND only after they have undergone a minimum of 3 shaker shatter resistance tests. In order to be considered an ND variety, the line must pass the ND threshold in multiple nurseries for multiple years.<br>Varieties which have sufficient seed retention to be classified as non-dehiscent have been previously disclosed by Sesaco in U.S. Patents U.S. Pat. Nos. 6,100,452; 6,815,576; 6,781,031; 7,148,403; and 7,332,652.<br>The K28p progenitor is a shattering line. Through breeding, homozygous py/py pygmy alleles have been joined to non-dehiscent alleles to produce non-dehiscent pygmy lines. Sixty-two (62) pygmy ND lines have been developed to date. | | | | | | |
| Improved non-dehiscent visual rating (Character 17) | K28p<br>Z | S25<br>6.2 | D51p<br>Z | S26<br>6.5 | D50p<br>Z | S27<br>7.2 | D54p<br>7.5 |
| | Amount of seed in most of the capsules in the plants in a plot four or more weeks after the ideal harvest time. The value is based on the average on a minimum of three plots of a subjective rating based on the percentage of capsules with visible seed retention<br>8 <100%<br>7 <85%<br>6 <70%<br>5 >55%<br>Z <55%<br>'*', '+' and '−' modifiers can be used. For averages, 0.5 is added for a '*', 0.33 is added for a '+', and 0.33 is subtracted for a '−', e.g., "7+" = 7.33.<br>The data is taken four or more weeks after the ideal harvest time by estimating the percentage of capsules that have visible seed at the top. In the beginning in order to develop an eye for the rating, the evaluator should observe all of the capsules and rate each of them; get a counts of those with no visible seeds (quicker to count those with visible seeds) and a count of total capsules; and compute a percentage. Once the evaluator is skilled, there is no need to count the capsules. There is a very high correlation between this rating upon visual evaluation and the amount of rattling generated by the "drum test". The "drum test" consists of placing the fingers from one hand about ½ inch from the center of the main stem and then striking the stem alternately with one finger and then the other finger in rapid succession. The human ear can perceive degree of rattling over a range. IND is defined as having no rattle. Degree of rattle in this test correlates with loss of increasing amounts of seed as capsules are exposed to weather conditions.<br>Although retention can vary from plant to plant and even within a plant, the overall rating is correlatable with IND.<br>The shattering lines (K28p, D50p, and D51p) and were not rated since a prerequisite for the test is non-shattering. S27 and D54p are the only lines used in the method disclosed herein that passed the IND test. | | | | | | |
| Improved non-dehiscent test (Character 18) | K28p<br>ZZ | S25<br>ZZ | D51p<br>ZZ | S26<br>ZZ | D50p<br>ZZ | S27<br>IND | D54p<br>IND |
| | An ND line that passes the rattle test and has a visual IND rating >6.99 is considered IND. A method for traditional breeding of an IND line is described in U.S. Patent Application Serial No12/041,257, filed Mar. 3, 2008 which is herein incorporated by reference as if set forth in its entirety.<br>ND and IND lines should not have id or gs alleles. Subjective rating based on the following values:<br>IND = Improved Non-dehiscent line<br>ZZ = Line that does not pass the improved non-dehiscent test<br>Using an IND parent does not guarantee an IND progeny particularly when crossing an IND with a shattering line. Now that the pygmy and IND genes have been joined, D54p was used as a parent to develop many other IND pygmies whether crossing it against normal IND or ND lines or with crossing it against pygmy IND or ND lines. Through this method, there have been 50 pygmy IND lines developed. | | | | | | |

TABLE VI-continued

Characters that Influence potential yield

| | | | | | | | |
|---|---|---|---|---|---|---|---|
| Lodging resistance (Character 19) | K28p NT | S25 5.0 | D51p NT | S26 5.3 | D50p NT | S27 6.7 | D54p 7.7 |

The amount of lodging. Average of a minimum of three plots of a subjective rating based on the following values:
0 to 8 rating
8 = no lodging
7 = Less than 5% of plants lodged
4 = 50% of plants lodged
1 = All plants lodged
Intermediate values are used.

There are three types of lodging: where the plants break at the stem, where the plants bend over but do not break, and where the plants uproot and bend over. When a plant breaks over, it will rarely produce any new seed, and the existing seed may or may not mature. If there is a total break, there is no hope, but if there is still some active stem translocation through the break, there can be some yield recovery. The main causes for uprooting of plants are shallow root systems and fields that have just been irrigated or after a heavy rain, creating a soft layer of soil. When a plant bends over early in development, some lines adapt better than others in terms of having the main stems turn up and continue flowering. The tips of the branches are usually matted under the canopy and will rarely turn up, but new branches can develop. As the plants go to drydown and the weight of the moisture is lost, many of the bent plants will straighten up making the crop easier to combine.

This is a character that can prevent yield if the field lodges early or lose yield if the field lodges late. When there is early lodging, the plants and leaves block the sun and reduce the amount of possible photosynthesis, but the winds can also break plants and/or branches. When there is late lodging, the winds can break plants and/or branches, and if the capsules are dry, the winds can shatter some of the capsules. Winds can also have another late effect - the rubbing of the plants against each other in the wind can rub off capsules. This rubbing normally is not a problem in early winds because the leaves act as shock absorbers.

The amount of resistance to lodging is directly correlated to stem strength. There are pygmy lines that will lodge and others that will not. However, the pygmies have two advantages that increase their resistance to lodging: (1) They are low to the ground and the wind speed is lower and (2) Being smaller they present less resistance to the wind. Experimental plots grown in the Uvalde nursery were subjected to 65 mph winds. Most of the pygmy sesame plants stayed upright including the D54p above. There was less lodging in the pygmy section of the nursery than in the normal section.

| | | | | | | | |
|---|---|---|---|---|---|---|---|
| Resistance to drought (Character 20) | K28p Good | S25 Poor | D51p Good | S26 Good | D50p Good | S27 Medium | D54p Good |

The relative amount of resistance to drought. An average of a minimum of 3 plots of a subjective rating based on the following values using a 0-8 scale:
7 = little negative effect from drought
4 = medium negative effect from drought
1 = considerable negative effect from drought
Intermediate values are used. Within Sesaco the values range from 0 to 8 with the average changing within nursery.

In a year when there is a drought, this rating can be used to differentiate the effects of the different lines. This is a highly subjective rating requiring a rater that is familiar with the performance of the line under normal conditions. The rating is based on how the drought changes the line from normal. Thus, a short line that does not change significantly in a drought may have a higher rating than a tall line which is affected by the drought even though the taller line is taller in the drought than the short line.

In the absence of droughts, the 0-8 scale cannot be used. In such case, a rating of poor, medium, good, and very good can be used as a subjective rating based on observation of the effects of a dry period between irrigations or rains.

Under test conditions where a third irrigation was delayed, the majority of the lines, showed severe wilting in the afternoon with some lines shedding their lower leaves In contrast, the pygmy lines showed no wilt. In another test nursery, pygmies and standard height varieties were grown on a steep slope that had less moisture. Again, the pygmies never shed their bottom leaves and yielded better than the standard height varieties. As a result, it is hypothesized that with a lower non-leaf harvest index, that the pygmies require less moisture and thus do better in low moisture conditions.

TABLE VI-continued

Characters that Influence potential yield

| | | | | | | | |
|---|---|---|---|---|---|---|---|
| Composite kill resistance (Character 21) | K28p 2.0 | S25 5.1 | D51p 2.9 | S26 4.9 | D50p 3.3 | S27 5.8 | D54p 3.5 |

The amount of plants killed by root rots in the Sesaco nurseries. Average of a minimum of three plots of a subjective rating based on the following values: Ratings are based on the number of plants killed in a plot. Before physiological maturity (PM), the following ratings are used:
1 = >90% kill before flower termination
2 = >90% kill between flower termination and PM. After PM, the following ratings are used:
3 = >90% kill
4 = 50 to 89% kill
5 = 25 to 49% kill
6 = 10 to 24% kill
7 = less than 10% kill
8 = no kill
On the week a plot reaches PM, a rating is assigned. The ratings are then taken for 2 additional weeks. The three ratings are averaged for a final kill rating. For example, if a plot has a final kill of 766, the average for the plot will be 6.33. When a value of 1 or 2 is assigned, there are no additional ratings and there is no averaging. Within Sesaco the range is from 1 to 8 with an average of 4.52.
There are three root diseases that affect sesame in Texas: *Fusarium oxysporum*, *Macrophomina phaseoli*, and *Phytophthora parasitica*. Between 1988 and the present, spores of these three have been accumulated in one small area (1 square km) north of Uvalde, and thus it is an excellent screening area for the diseases. Although each root rot attacks sesame in a different way with different symptoms, no effort is made to differentiate which disease is the culprit in each plot. Pathological screenings in the past have found all 3 pathogens present in dead plants. The comparison above is from a nursery with severe kill, and all seven lines were compared. In one test, the ratings were as follows: K28p = 2.0, S25 = 6.4, S26 = 7.0, S27 7.3, and D54p 6.8. Despite the low rating of the progenitor K28p, it has been possible to select for improved kill resistance in some of the progeny such as D54p.

| | | | | | | | |
|---|---|---|---|---|---|---|---|
| Resistance to silverleaf whitefly (*Bemisia argentifolii*) (Character 22) | K28p Poor | S25 Good | D51p Medium | S26 Very good | D50p Medium | S27 Good | D54p Medium |

Amount of resistance to the silverleaf whitefly. Average of a minimum of three plots of a subjective rating based on the following values using a 0 to 8 scale of the % of infected plants:
8 = Zero insects
7 = Few insects
4 = Many insects
1 = Insects killing the plants
Intermediate values are used.
NT = not tested
NEC = no economic damage - not enough insects to do ratings
Ratings can be done in several ways:
1. Take ratings after the insects are no longer increasing.
2. Take ratings on consecutive weeks until insects are no longer increasing and average ratings.
3. Take periodic ratings and average ratings.
There have been some years (1991-1995) where the incidence of silverleaf whitefly has significantly affected nurseries and commercial crops. In most years, a few white flies can be seen in the sesame with no economic damage, possibly due to introduction of natural predators of the silverleaf whitefly in crop locations, or to natural tolerance to whitefly in the newer sesame varieties. Higher temperatures decrease the number of days between generations and higher moisture and fertility have been implicated as possible causes for the increase the incidence of whiteflies. In the absence of severe infestations, the 0-8 scale cannot be used In such case, a rating of poor, medium, good, and very good are a subjective rating based on the relative amount of infestation.
The progenitor K28p is very susceptible to whiteflies. In the nurseries there is more damage from whitefly to the pygmy lines, but filtering for resistance has reduced the problem considerably.

| | | | | | | | |
|---|---|---|---|---|---|---|---|
| Resistance to green peach aphid (*Myzus persica*) (Character 23) | K28p 2.0 | S25 8.0 | D51p 2.2 | S26 8.0 | D50p 7.1 | S27 8.0 | D54p 4.4 |

Amount of resistance to the green peach aphid. The rating system is the same as for the Resistance to silverleaf whitefly (Character No. 22).
There have been some years (1990-1995) where the incidence of green peach aphid has affected nurseries or commercial crops. In most years, a few aphids can be seen in the sesame with no economic damage.
Unlike the whitefly where only the southern portion of the US sesame growing area is affected, the green peach aphid has been seen into Southern Oklahoma, but it has been rare. The only commercial fields that have been affected are planted late and with very susceptible varieties. The green peach aphid attacks pecan groves and the only commercial

TABLE VI-continued

Characters that Influence potential yield

| | | | | | | | |
|---|---|---|---|---|---|---|---|
| | fields that have been affected are near pecan groves. In 1992 there was a severe attack on a breeding nursery in San Angelo, Texas, and hundreds of breeding lines were discontinued and resistant lines were accelerated. However, aphids are present in most years and Sesaco maintains "canary" lines in the nurseries to detect the insect. A canary line is very susceptible to the disease or insect. In 2004, the pygmy lines became the canary lines, and there began considerable filtering for resistance.<br>The progenitor K28p is very susceptible to the green peach aphid. In the nurseries there is more damage from green peach aphid to the pygmy lines, but filtering for resistance has reduced the problem considerably. | | | | | | |
| Dry pod on a green stem (Character 24) | K28p<br>Yes | S25<br>No | D51p<br>No | S26<br>No | D50p<br>No | S27<br>No | D54p<br>No |
| | Dry pod on a green stem (DPGP) was a very common trait on lines from Asia, but in recent years, breeders in many countries have selected away from this trait, and introductions seldom show the problem. The trait occurs when there are dry capsules on a plant that still has leaves and flowers. In severe cases, there can be a dry capsule on a leaf axil that has not shed its leaf.<br>In a manual harvest environment, DPGP is not a desirable character because the practice is to cut the plants as soon as dry capsules appear and shock the plants to dry. The leaves delay drying and generally the seed towards the top of the plant has not filled. In a mechanical harvest environment, DPGP is not as serious a problem because the harvest cannot be done until the plant is dry, but it does mean that there are dry capsules on the plants longer than necessary. No matter the degree of shatter resistance, there is some loss of seed, and the longer the dry capsule is exposed to the elements, the greater the amount of seed loss. The ideal is to have all the seed to the top of the plant filled and the leaves off the plant before the first dry capsule and all Sesaco varieties have this trait.<br>DPGP is such an easy trait to select away from that the genetics of the trait has not been studied. By the F3 of a cross between a DPGP line and a normal line, the trait has been eliminated. However, it is included in this list because the progenitor K28p had a severe case of DPGP. | | | | | | |

I claim:

1. A method for producing a pygmy sesame crop, comprising the steps of:
    (a) planting a pygmy sesame seed line, wherein said pygmy sesame seed line is homozygous for the pygmy allele designated py/py, wherein said py/py homozygous recessive allele is described in sesame variety S70, a sample of said sesame seed variety S70 is deposited under ATCC Accession number PTA-9272, and said pygmy sesame seed line produces pygmy sesame plants with a mature plant height greater than 52 cm and less than 120 cm, said mature pygmy sesame plants produced by said pygmy sesame seed line have one or more capsules at a height of at least 15 cm; and
    (b) harvesting said mature pygmy sesame plants from said pygmy sesame seed line, said pygmy sesame plants exhibiting a higher harvest index on a weight basis than plants with non-pygmy sesame crops wherein said harvest index is the ratio of weight of the harvested seed to the weight of the entire plant including seed.

2. The method of claim 1, wherein said pygmy sesame seed line is planted at 10 to 20 sesame plants per linear meter in a planting row.

3. The method of claim 1, wherein said pygmy sesame seed line is planted in rows 20 cm to 40 cm apart.

4. The method of claim 1, wherein said pygmy sesame seed line is planted in rows from 15 cm to 20 cm apart.

5. The method of claim 1, wherein said mature pygmy sesame plants have a mature height between 84 cm and 110 cm.

6. The method of claim 1, wherein said mature pygmy sesame plants have one or more capsules at a height from 15 cm to 30 cm.

7. The method of claim 1, wherein said one or more capsules on said pygmy sesame plants have greater adhesion between the false membranes leading to said higher harvest index on a weight basis than non-pygmy sesame plants.

8. The method of claim 1, wherein said one or more capsules on said pygmy sesame plants have greater placenta attachment leading to said higher harvest index on a weight basis than non-pygmy sesame plants.

9. The method of claim 1, wherein said one or more capsules on said pygmy sesame plants have more seed in capsules leading to said higher harvest index on a weight basis measured four weeks after said pygmy sesame crop is ready for harvest than non-pygmy sesame plants.

10. A method for producing a pygmy sesame crop, comprising:
    planting a pygmy sesame seed line, wherein said pygmy sesame seed line is homozygous for the pygmy allele designated py/py, py/py, wherein said py/py homozygous recessive allele is described in sesame variety S70, a sample of said sesame seed variety S70 is deposited under ATCC Accession number PTA-9272, and said pygmy sesame seed line produces pygmy sesame plants with a mature plant height greater than 52 cm and less than the height of non-pygmy sesame plants and said mature pygmy sesame plants produced by said pygmy sesame seed line have one or more capsules at a height of at least 15 cm.

11. The method of claim 10, further comprising the step of:
    harvesting said mature pygmy sesame plants from said pygmy sesame seed line, said pygmy sesame plants exhibiting a greater number of seeds in capsules than non-pygmy sesame plants.

12. The method of claim 10, wherein said pygmy sesame seed line is planted 10 to 20 sesame plants per linear meter in a planting row.

13. The method of claim 10, wherein said pygmy sesame seed line is planted in rows from 20 cm to 40 cm apart.

14. The method of claim 10, wherein said pygmy sesame seed line is planted in rows from 15 cm to 20 cm apart.

15. The method of claim 10, wherein said mature pygmy sesame plants have a mature height between 84 cm and 110 cm.

16. The method of claim 10, wherein said mature pygmy sesame plants have one or more capsules at a height from 15 cm to 30 cm.

17. The method of claim 10, wherein said one or more capsules on said pygmy sesame plants have greater adhesion between the false membranes leading to a higher harvest index on a weight basis than non-pygmy sesame plants.

18. The method of claim 10, wherein said one or more capsules on said pygmy sesame plants have greater placenta attachment leading to a higher harvest index on a weight basis than non-pygmy sesame plants.

19. The method of claim 10, wherein said one or more capsules on said pygmy sesame plants have more seed in capsules leading to a higher harvest index on a weight basis measured four weeks after said pygmy sesame crop is ready for harvest than non-pygmy sesame plants.

20. A method for producing a pygmy sesame crop, comprising the steps of:
   (a) planting a pygmy sesame seed line, wherein said pygmy sesame seed line is homozygous for the pygmy allele designated py/py, wherein said py/py homozygous recessive allele is described in sesame variety S70, a sample of said sesame seed variety S70 is deposited under ATCC Accession number PTA-9272, and said pygmy sesame seed line produces pygmy sesame plants with a mature height between 84 cm and 110 cm, and having a first capsule height of 15 cm to 30 cm; and
   (b) harvesting said mature pygmy sesame plants from said pygmy sesame seed line, said pygmy sesame plants exhibiting a higher harvest index on a weight basis than plants with non-pygmy sesame crops wherein said harvest index is the ratio of weight of the harvested seed to the weight of the entire plant including seed.

21. The method of claim 20, wherein said pygmy sesame seed line is planted at 10 to 20 sesame plants per linear meter in a planting row.

22. The method of claim 20, wherein said pygmy sesame seed line is planted in rows from 20 cm to 40 cm apart.

23. The method of claim 20, wherein said pygmy sesame seed line is planted in rows from 15 cm to 20 cm apart.

24. The method of claim 20, wherein said one or more capsules on said pygmy sesame plants have greater adhesion between the false membranes leading to said higher harvest index on a weight basis than non-pygmy sesame plants.

25. The method of claim 20, wherein said one or more capsules on said pygmy sesame plants have greater placenta attachment leading to said higher harvest index on a weight basis than non-pygmy sesame plants.

26. The method of claim 20, wherein said one or more capsules on said pygmy sesame plants have more seed in capsules leading to said higher harvest index on a weight basis measured four weeks after said pygmy sesame crop is ready for harvest than non-pygmy sesame plants.

27. The method of claim 1, wherein said mature pygmy sesame plants have a capsule zone length from 18 cm to 81 cm, said capsule zone length extending from the bottom of the lowest capsule on the main stem to the top of the highest capsule with viable seed on the main stem.

28. The method of claim 10, wherein said mature pygmy sesame plants have a capsule zone length from 18 cm to 81 cm, said capsule zone length extending from the bottom of the lowest capsule on the main stem to the top of the highest capsule with viable seed on the main stem.

29. The method of claim 20, wherein said mature pygmy sesame plants have a capsule zone length from 18 cm to 81 cm, said capsule zone length extending from the bottom of the lowest capsule on the main stem to the top of he highest capsule with viable seed on the main stem.

\* \* \* \* \*

UNITED STATES PATENT AND TRADEMARK OFFICE
CERTIFICATE OF CORRECTION

| | | |
|---|---|---|
| PATENT NO. | : 8,993,835 B2 | Page 1 of 1 |
| APPLICATION NO. | : 14/191732 | |
| DATED | : March 31, 2015 | |
| INVENTOR(S) | : Derald Ray Langham | |

It is certified that error appears in the above-identified patent and that said Letters Patent is hereby corrected as shown below:

In the Claims

Col. 30, Claim 10, line 5, delete "py/py" before "wherein"
Col. 32, Claim 29, line 4, change "of he highest" to --of the highest--

Signed and Sealed this
Eleventh Day of August, 2015

Michelle K. Lee
*Director of the United States Patent and Trademark Office*